United States Patent
Chen et al.

(10) Patent No.: US 10,856,735 B2
(45) Date of Patent: Dec. 8, 2020

(54) OPTICAL COHERENCE TOMOGRAPHY (OCT) SYSTEM WITH IMPROVED IMAGE QUALITY

(71) Applicant: UNIVERSITY OF SOUTHERN CALIFORNIA, Los Angeles, CA (US)

(72) Inventors: Yu Chen, Irvine, CA (US); Scott E. Fraser, Glendale, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 0 days.

(21) Appl. No.: 16/465,070

(22) PCT Filed: Nov. 27, 2017

(86) PCT No.: PCT/US2017/063283
§ 371 (c)(1),
(2) Date: May 29, 2019

(87) PCT Pub. No.: WO2018/102255
PCT Pub. Date: Jun. 7, 2018

(65) Prior Publication Data
US 2019/0380574 A1      Dec. 19, 2019

Related U.S. Application Data

(60) Provisional application No. 62/428,055, filed on Nov. 30, 2016.

(51) Int. Cl.
*G01B 9/02*      (2006.01)
*G06T 5/00*      (2006.01)
(Continued)

(52) U.S. Cl.
CPC ............ *A61B 3/102* (2013.01); *A61B 3/12* (2013.01); *A61B 3/14* (2013.01); *A61B 3/152* (2013.01);
(Continued)

(58) Field of Classification Search
CPC ............ G01B 9/02091; G01B 9/02041; G01B 9/02083; G01B 9/02085; G01B 9/02087;
(Continued)

(56) References Cited

U.S. PATENT DOCUMENTS 5,799,111 A *   8/1998   Guissin ................. H04N 19/86
                                                      358/447
8,694,266 B2*  4/2014   Mycek ................. A61B 5/0071
                                                      702/19
(Continued)

FOREIGN PATENT DOCUMENTS

JP      2016035402 A       3/2016
WO     WO 2015/134571 A1   9/2015

OTHER PUBLICATIONS

International Search Report for PCT Application No. PCT/US2017/063283, dated Feb. 16, 2018, 3 pages.
(Continued)

*Primary Examiner* — Jonathan M Hansen
(74) *Attorney, Agent, or Firm* — McDermott Will & Emery LLP

(57) ABSTRACT

This disclosure relates to the field of Optical Coherence Tomography (OCT). This disclosure particularly relates to an OCT system that generates an image with improved quality. In one example, the OCT system may generate an improved Bscan image by using multiple shaping functions to shape the raw A-scans. In another example, the OCT system may generate the improved B-scan image by forming multiple apodization patterns on a detector and acquiring raw A-scans by using the apodization patterns. A better diagnosis of a health condition may be reached by using the improved images generated by the OCT system of this disclosure.

16 Claims, 23 Drawing Sheets

(51) Int. Cl.
    *A61B 3/10*      (2006.01)
    *A61B 3/12*      (2006.01)
    *A61B 3/14*      (2006.01)
    *A61B 3/15*      (2006.01)
(52) U.S. Cl.
    CPC .......... *G01B 9/02091* (2013.01); *G06T 5/002* (2013.01); *G06T 2207/10101* (2013.01); *G06T 2207/30041* (2013.01)
(58) Field of Classification Search
    CPC ............ G01B 9/02088; G01B 9/02089; A61B 3/102; G06T 5/002
    See application file for complete search history.

(56) References Cited

U.S. PATENT DOCUMENTS

| | | | |
|---|---|---|---|
| 9,324,141 B2 | 4/2016 | Begin | |
| 2011/0268328 A1* | 11/2011 | Bar-Aviv | G06T 5/002 382/128 |
| 2012/0320368 A1 | 12/2012 | Jiao et al. | |
| 2015/0062590 A1 | 3/2015 | Bagherinia | |

OTHER PUBLICATIONS

Extended European Search Report dated May 12, 2020 in European Patent Application No. 17876880.0.
Chen, Yu, et al. "Multi-shaping technique reduces sidelobe magnitude in optical coherence tomography" Biomedical optics Express, vol. 8, No. 11, pp. 5267-5281, Oct. 26, 2017.
International Preliminary Report on Patentability dated Jun. 4, 2019 in PCT Application No. PCT/US2017/063283.

\* cited by examiner

OPTICAL COHERENCE TOMOGRAPHY (OCT) SYSTEM WITH IMPROVED IMAGE QUALITY

CROSS-REFERENCE TO RELATED APPLICATION

This application is a U.S. National Phase Application of International Application No. PCT/US2017/063283, entitled "An Optical Coherence Tomography (OCT) System With Improved Image Quality," filed on Nov. 27, 2017, which based upon and claims the benefit of priority to U.S. Provisional Patent Application No. 62/428,055, entitled "Optical Coherence Tomography (OCT) System With Improved Image Quality," filed Nov. 30, 2016, the complete contents of both which are incorporated herein by reference.

BACKGROUND

Technical Field

This disclosure relates to the field of Optical Coherence Tomography (OCT). This disclosure particularly relates to an OCT system with improved image quality. This disclosure further relates to an OCT system that is used in diagnosing a health condition.

Description of Related Art

Optical coherence tomography (OCT) has become an indispensable clinical imaging tool, since its introduction in 1991. For a background of OCT technology, see, for example, Drexler and Fujimoto et al. "Optical Coherence Technology: Technology and Applications" Springer, Heidelberg, Germany, 2008. This book is incorporated herein by reference in its entirety. OCT is based on an optical measurement technique known as low-coherence interferometry. OCT performs high resolution, cross-sectional imaging of the internal microstructure of a physical object by directing a light beam to the physical object, and then measuring and analyzing the magnitude and time delay of backscattered light.

A cross-sectional image is generated by performing multiple axial measurements of time delay (axial scans or A-scans) and scanning the incident optical beam transversely. This produces a two-dimensional data set of B-scans comprising A-scans; which represents the optical backscattering in a cross-sectional plane through the physical object. Three-dimensional, volumetric data sets can be generated by acquiring sequential cross-sectional images by scanning the incident optical beam in a raster pattern (three-dimensional OCT or 3D-OCT). This technique yields internal microstructural images of the physical objects with very fine details. For example, pathology of a tissue can effectively be imaged in situ and in real time with resolutions smaller than 15 micrometers.

Several types of OCT systems and methods have been developed, for example, Time-Domain OCT (TD-OCT) and Fourier-Domain OCT (FD-OCT). Use of FD-OCT enables high-resolution imaging of retinal morphology that is nearly comparable to histologic analysis. Examples of FD-OCT technologies include Spectral-Domain OCT (SD-OCT) and Swept-Source OCT (SS-OCT).

OCT may be used for identification of common retinovascular diseases, such as age-related macular degeneration (AMD), diabetic retinopathy (DR), and retinovascular occlusions. However, despite the rapid evolution of OCT imaging, current OCT technology may not provide adequate visualization of retinal and choroidal microvasculature. Thus, clinicians are often compelled to order both OCT and fluorescein angiography (FA) in patients with the retinovascular diseases. There has been increased interest in using data generated during FD-OCT imaging to generate angiographic images of the fundus. These angiograms are implemented noninvasively without injection of fluorescent dye.

For further description of OCT methods and systems, and their applications, for example, see: Schwartz et al. "Phase-Variance Optical Coherence Tomography: A Technique for Noninvasive Angiography" American Academy of Ophthalmology, Volume 121, Issue 1, January 2014, Pages 180-187; Sharma et al. "Data Acquisition Methods for Reduced Motion Artifacts and Applications in OCT Angiography" U.S. Pat. No. 8,857,988; Narasimhalyer et al. "Systems and Methods for Improved Acquisition of Ophthalmic Optical Coherence Tomography Data" U.S. Patent Application Publication No. 2014/0268046; Everett "Methods for Mapping Tissue With Optical Coherence Tomography Data" U.S. Pat. No. 7,768,652. The entire content of each of these publications and patent disclosures is incorporated herein by reference.

In OCT, one major type of artifact is sidelobe noise in the axial direction, which severely degrades the quality of B-scan images. The axial point spread function (PSF), also referred as the coherence function, is proportional to the Fourier transform of the light source spectrum. When the spectrum of light source or the detected spectrum is non-Gaussian shape, as it is usually the case for broadband light sources, high sidelobes will be present in B-scan images. A number of shaping methods have been used to shape the non-Gaussian spectra in OCT imaging, such as Gaussian fit, Gaussian and Hamming windowing functions, in order to suppress axial sidelobes. However, all these methods are at the expense of worsening the axial resolution with a widened mainlobe in the axial PSF.

For further description of shaping methods in OCT imaging, and their applications, for example, see: Tripathi et al. "Spectral shaping for non-Gaussian source spectra in optical coherence tomography" Optics Letters, Volume 27, Issue 6, March 2002, Pages 406-408; Akcay et al. "Spectral shaping to improve the point spread function in optical coherence tomography" Optics Letters, Volume 28, Issue 20, October 2003, Pages 1921-1923; Lee et al. "Ultrahigh speed spectral-domain optical coherence microscopy" Biomedical Optics Express, Volume 4, Issue 8, August 2013, Pages 1236-1254. The entire content of each of these publications and patent disclosures is incorporated herein by reference.

SUMMARY

This disclosure relates to the field of Optical Coherence Tomography (OCT). This disclosure particularly relates to an OCT system with improved image quality. This disclosure further relates to an OCT system that is used in diagnosing a health condition.

In this disclosure, the OCT system may generate an improved B-scan image of a target. The OCT system may comprise an optical system, an image generation system, or a combination thereof. For example, the OCT system may comprise an optical system and an image generation system. For example, the OCT system may comprise an image generation system.

In this disclosure, the optical system may comprise an optical component. Examples of such optical component includes an illumination source, a beam splitter, a reference arm, a target arm, an optical detection system, or a combination thereof. In this disclosure, the optical detection system may include an optical component such as a detector. In this disclosure, the optical detection system may include an optical component such as a spectrometer. In this disclosure, the spectrometer may comprise a detector. The detector may comprise at least 3 pixels, 100 pixels, 1,000 pixels, or 2,000 pixels. In this disclosure, such pixels of the detector are referred as "detector pixels".

In this disclosure, the OCT system may include a spectral domain optical coherence tomography (SD-OCT) system.

In this disclosure, the OCT system may include an optical grating, a first optical lens between the beam splitter and the grating, and a second optical lens between the optical grating and the detector; and wherein the first lens, the grating and the second lens have a configuration that projects an interfered light beam formed by the beam splitter on the at least three pixels.

In this disclosure, the image generation system may comprise a control unit, a processing unit, a memory unit, a display unit, or a combination thereof.

In this disclosure, the OCT system may have a configuration that illuminates and scans the target.

In this disclosure, the OCT system may have a configuration that forms or acquires discretized OCT interference spectra.

In this disclosure, each (raw or shaped) B-scan may comprise at least one (raw or shaped) A-scan. In this disclosure, each (raw or shaped) B-scan may comprise at least two (raw or shaped) A-scans.

In this disclosure, the OCT system may have a configuration that generates or acquires raw A-scan and/or raw B-scan based on the generated or the acquired discretized OCT interference spectra.

In this disclosure, the OCT system may have a configuration that shapes each raw A-scan by using at least two different shaping functions for each raw A-scan to form at least two shaped A-scans for each raw A-scan.

In this disclosure, the OCT system may have a configuration that forms/acquires at least two B-scans ("shaped B-scan"). The shaped A-scans forming the same shaped B-scan may be shaped with the same shaping function.

In this disclosure, the OCT system may have a configuration that forms sets of detector pixels. Each detector pixel set may comprise at least one detector pixel. Each detector pixel set may comprise at least two detector pixels. The detector pixels forming the same detector pixel set may be adjacent to each other.

In this disclosure, the OCT system may have a configuration that forms discretized OCT interference spectra on each detector pixel.

In this disclosure, the OCT system may have a configuration that generates/acquire at least two (raw) A-scans. Each (raw) A-scan may be generated/acquired from the discretized OCT interference spectra formed on each detector pixel.

In this disclosure, the OCT system may have a configuration that determines a maximum intensity of each shaped B-scan.

In this disclosure, the OCT system may have a configuration that normalizes each shaped B-scan ("normalized B-scan") by using the maximum intensity of the same shaped B-scan.

In this disclosure, the OCT system may have a configuration that selects one pixel for each normalized shaped B-scan ("B-scan pixel").

In this disclosure, the OCT system may have a configuration that processes intensity values of selected B-scan pixels of all normalized shaped B-scans by using a mathematical operation, wherein the selected B-scan pixels have the same position on all normalized shaped B-scans, and wherein the all normalized shaped B-scan belong to the same multi-shaped B-scan image cluster.

In this disclosure, the OCT system may have a configuration that forms sets of pixels. Each pixel set may comprise one pixel ("B-scan pixel") from each normalized B-scan. The B-scan pixels of each pixel set may have the same position on all normalized B-scans.

In this disclosure, the OCT system may have a configuration that determines one intensity ("optimized intensity") for each pixel set by applying a mathematical operation to intensities of pixels forming the same pixel set. The mathematical operation may comprise a rank order filter, a mean filter, a multi-image deconvolution, or a combination thereof.

In this disclosure, the OCT system may have a configuration that generates a new B-scan ("new B-scan") based on the optimized intensities of the pixel sets.

In this disclosure, the OCT system may have a configuration that displays the improved B-scan image on the image generation system's display.

In this disclosure, the shaping function may include a function that is zero-valued outside of a chosen interval. The shaping function may include a window function, a Gaussian function, or a combination thereof.

In this disclosure, the mathematical operation may include a rank order filter. The rank order filter may be a minimum filter, a median filter, a rank order filter that has a rank between that of the minimum filter and the median filter, or a combination thereof. The mathematical operation may include a mean filter. The mean filter may include an arithmetic mean, a weighted mean, a geometric mean, a harmonic mean, a quadratic mean, a logarithmic mean, or a combination thereof. Any combination of these mathematical operations is within the scope of this disclosure.

In this disclosure, the OCT system may have a configuration that smooths the new B-scan by using a digital smoothing filter. The smoothing filter may include a linear smoothing filter, a non-linear smoothing filter, or a combination thereof. The smoothing filter may include a median filter, a Gaussian filter, or a combination thereof. Any combination of these filters is within the scope of this disclosure.

In this disclosure, the target may include any physical object. The physical object has a surface and a depth. For example, of the physical object may be an organic tissue. For example, the organic tissue may include a human eye. For example, the target may include a retina. For example, the target may include a fundus of an eye.

In this disclosure, the OCT system may, when said OCT system is incorporated to an image generation system, the OCT system may cause the image generation system to generate a new B-scan.

Any combination of methods, devices, components, systems, and features disclosed above is within the scope of this disclosure.

These, as well as other components, steps, features, objects, benefits, and advantages, will now become clear from a review of the following detailed description of illustrative embodiments, the accompanying drawings, and the claims.

BRIEF DESCRIPTION OF DRAWINGS

The drawings are of illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all of the components or steps that are illustrated. When the same numeral appears in different drawings, it refers to the same or like components or steps.

The following reference numerals are used for the system features disclosed in the following figures: optical coherence tomography system 100, optical system 105, illumination source 110, beam splitter 120, (optical) detection system 125, (optical) detector 130, image generation system 140, reference arm 150, target arm 160, target (physical object) 170, control unit 180, processing unit 190, memory unit 195, display unit 200, optical fiber 210, optical lens 220, optical lens 230, reflector 240, reference light beam 250, scanning mirror 260, scanning optics 270, collected light beam 280, cornea 290, choroid 300, vitreous chamber 310, pupil 320, retinal blood vessels 330, fovea region 340, optic nerve 350, optic disk 360, retina 370, fovea 380, nerve fiber layer 390, external limiting membrane 400, inner/outer photoreceptor segment 410, outer photoreceptor segment 420, retinal pigment epithelium 430, retinal pigment epithelium/Bruch's membrane complex 440, dispersion component 450, spectrometer 460, first optical lens 470, optical grating 480, and second optical lens 490.

DETAILED DESCRIPTION OF ILLUSTRATIVE EMBODIMENTS

Figure 1:
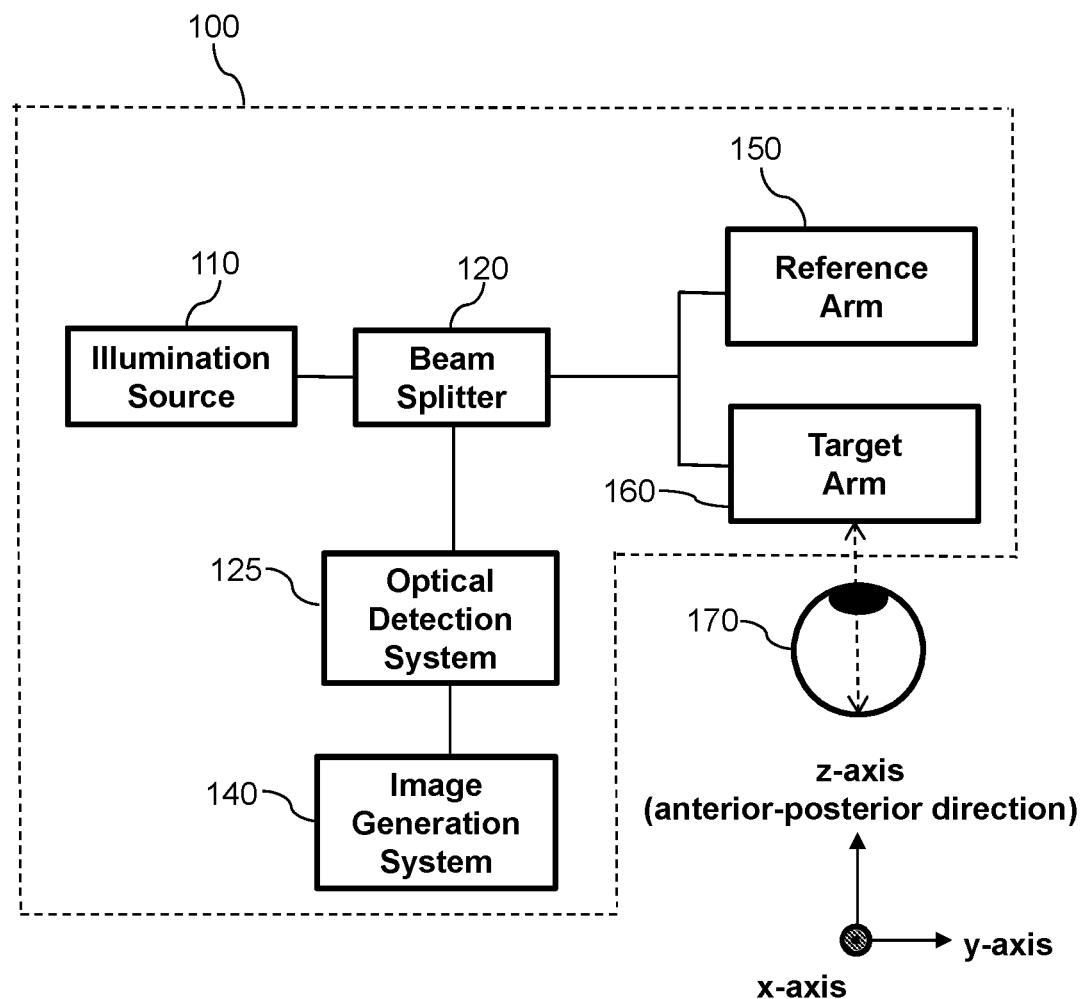
FIG. 1 is schematics of an exemplary generalized OCT system.

Illustrative embodiments are now described. Other embodiments may be used in addition or instead. Details that may be apparent or unnecessary may be omitted to save space or for a more effective presentation. Some embodiments may be practiced with additional components or steps and/or without all of the components or steps that are described.

This disclosure relates to the field of Optical Coherence Tomography (OCT). This disclosure particularly relates to an OCT system that can generate improved images. This disclosure further relates to an OCT system that is used in diagnosing a health condition.

This disclosure relates to an OCT system. The OCT system may include any interferometer that have any optical design comprising, such as Michelson interferometer, Mach-Zehnder interferometer, Gires-Tournois interferometer, common-path based designs, or other interferometer architectures. These interferometers may comprise a target arm and a reference arm. The target arm or the reference arm may comprise any type of optics, for example, bulk-optics, fiber-optics, hybrid bulk-optic systems, the like, or a combination thereof.

The OCT system may comprise any OCT system. Examples of the OCT system may include Time-domain OCT (TD-OCT), and Fourier-domain or Frequency-domain OCT (FD-OCT). Examples of the FD-OCT may include Spectral-domain OCT (SD-OCT), Swept Source OCT (SS-OCT), Optical frequency domain Imaging (OFDI), the like, or a combination thereof.

The OCT system may generate an improved B-scan image of a target. The OCT system 100 may comprise an optical (or optics) system 105, an image generation system 140, or a combination thereof. For example, the OCT system may comprise an optical system and an image generation system. For example, the OCT system may comprise an image generation system.

In this disclosure, the optical system may comprise an illumination source 110, a beam splitter 120, a reference arm 150, a target arm 160, an optical detection system 125, or a combination thereof.

In this disclosure, the image generation system 140 may comprise a control unit 180, a processing unit 190, a memory unit 195, a display unit 200, or a combination thereof.

An exemplary OCT system is shown in FIG. 1. This exemplary OCT system 100 may comprise at least one illumination source 110, at least one beam splitter 120, at least one (optical) detection system 125, at least one image generation system 140, at least one reference arm 150, and at least one target arm 160. This OCT system may scan and illuminate a target 170 that has a surface and a depth. It may form discretized OCT interference spectra from the scan by using the detection system, thereby generating raw A-scan data and raw B-scan data. This OCT system may generate an improved B-scan image by using the image generation system.

In this disclosure, the at least one illumination source 110 may comprise any source that can generate an electromagnetic wave at any wavelength. For example, the illumination source may by any light source. For example, the illumination source may be a low coherent light source. The illumination source may be either a broadband low coherence light source with short temporal coherence length in the case of SD-OCT, or a wavelength tunable laser source in the case of SS-OCT.

In this disclosure, light from the illumination source 110 may typically be guided by using at least one optical fiber 210 to the reference arm 150 and at least one optical fiber 210 to the target arm 160 to illuminate the target 170. The optical fiber may also guide light reflected from the reference arm and light scattered from the target to the detector through the beam splitter.

In this disclosure, the OCT system 100 may comprise any beam splitter 120 that can split and guide the light provided by the light source 110 to a reference arm 150 and a target arm 160.

Figure 2:
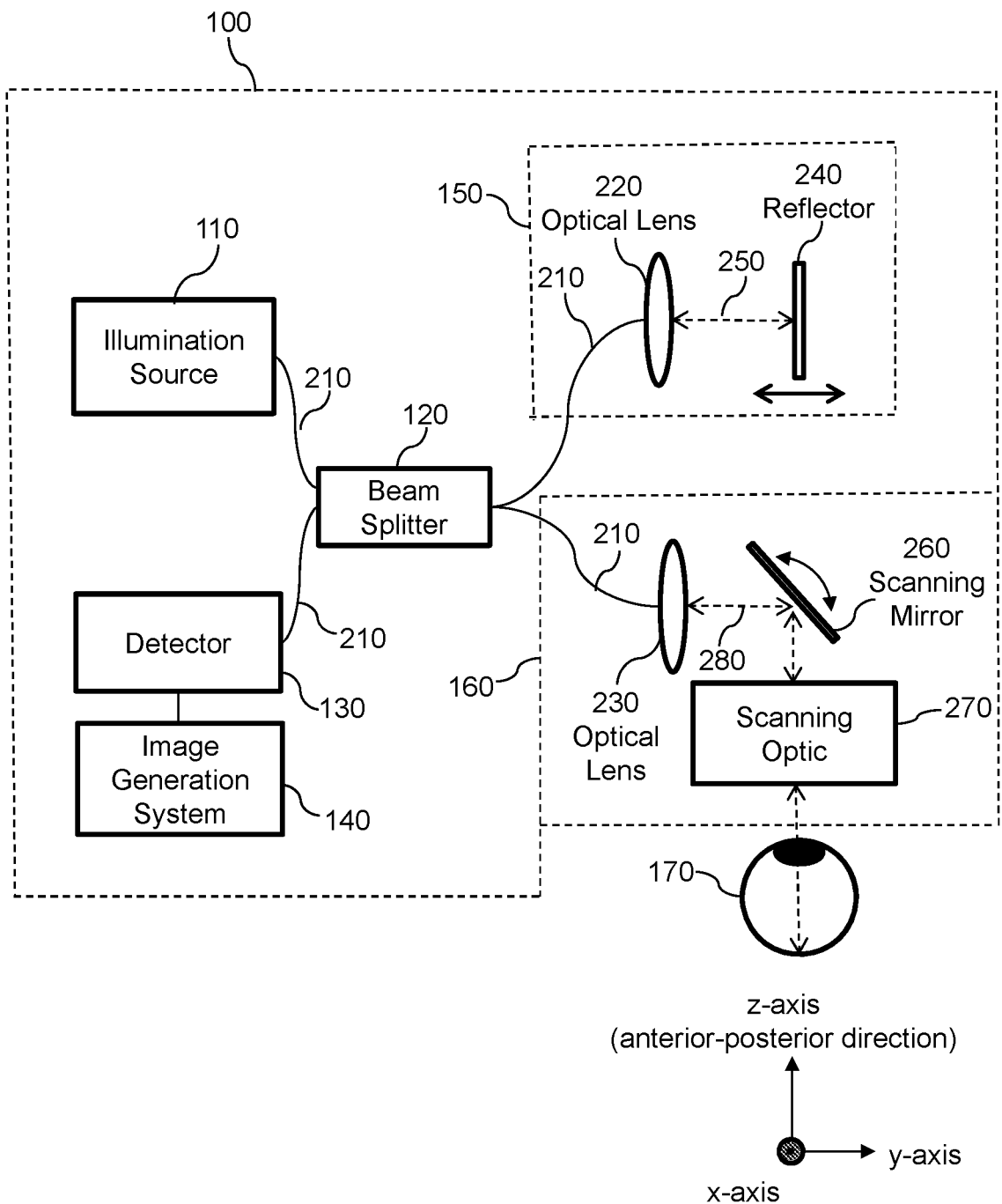
FIG. 2 is schematics of an exemplary generalized OCT system.

In this disclosure, an exemplary reference arm 150 may comprise at least one optical lens 220 and at least one reflector 240, as shown in FIG. 2. The optical lens may be placed between the reflector and the beam splitter.

In this disclosure, reference light beam 250 derived from the same illumination source 110 may travel a separate path, in this case involving the optical fiber 210 and the (retro-) reflector 240 with an adjustable optical delay. The reflector may be any reflector that can reflect light back to the optical lens. The reflector 240 may comprise at least one optical component. The at least one optical component of the reflector 240 may be, for example, a reference mirror.

In this disclosure, a transmissive reference path may also be used and the adjustable delay may be placed in the target arm 160 or the reference arm 150 of the interferometer 100.

In this disclosure, an exemplary target arm 160 may comprise at least one optical lens 230, at least one scanning mirror 260, and at least one scanning optic 270, as shown in FIG. 2. The light may be scanned, typically with the scanning optic 270 placed between the output of the optical fiber 220 and the target 170, so that a beam of light (dashed line) guided for the target 170 is scanned laterally (in x-axis and/or y-axis) over the area or volume to be imaged. The scanning optics 270 may comprise any optical element suitable for scanning. The scanning optics 270 may comprise at least one optical component. The at least one optical component of the scanning optics 270 may be any optical component. Light scattered from the target 170 may be collected, typically into the same optical fiber 210 used to guide the light for the illumination of the target. The target 170 is shown in the figures only to schematically demonstrate the target's 170 relation to the OCT system 100. The target is not a component of the OCT system.

In this disclosure, the optical detection system 125 may be any optical detection system. For example, the optical detection system may be a detector 130. For example, the optical detection system may be a spectrometer 460. For example, the optical detection system may be a balanced detection system. A combination of such exemplary optical detection systems is also within the scope of this disclosure. The optical detection system may include a fiber coupler.

In this disclosure, collected light 280 scattered from the target 170 may be combined with reference light 250, typically in a fiber coupler to form light interference in the optical detection system 125, thereby forming an OCT signal. Although a single optical fiber port is shown going to the optical detection system 125, various designs of the OCT system 100 may be used for balanced or unbalanced detection of the interference signal for SS-OCT or a spectrometer 460 for SD-OCT. Light beam as used herein should be interpreted as any carefully directed light path. In time-domain OCT systems, the reference arm 150 may need to have a tunable optical delay to generate interference. Balanced detection systems may typically be used in TD-OCT and SS-OCT systems, while spectrometers 460 may be used at the detection port for SD-OCT systems.

Figure 3:
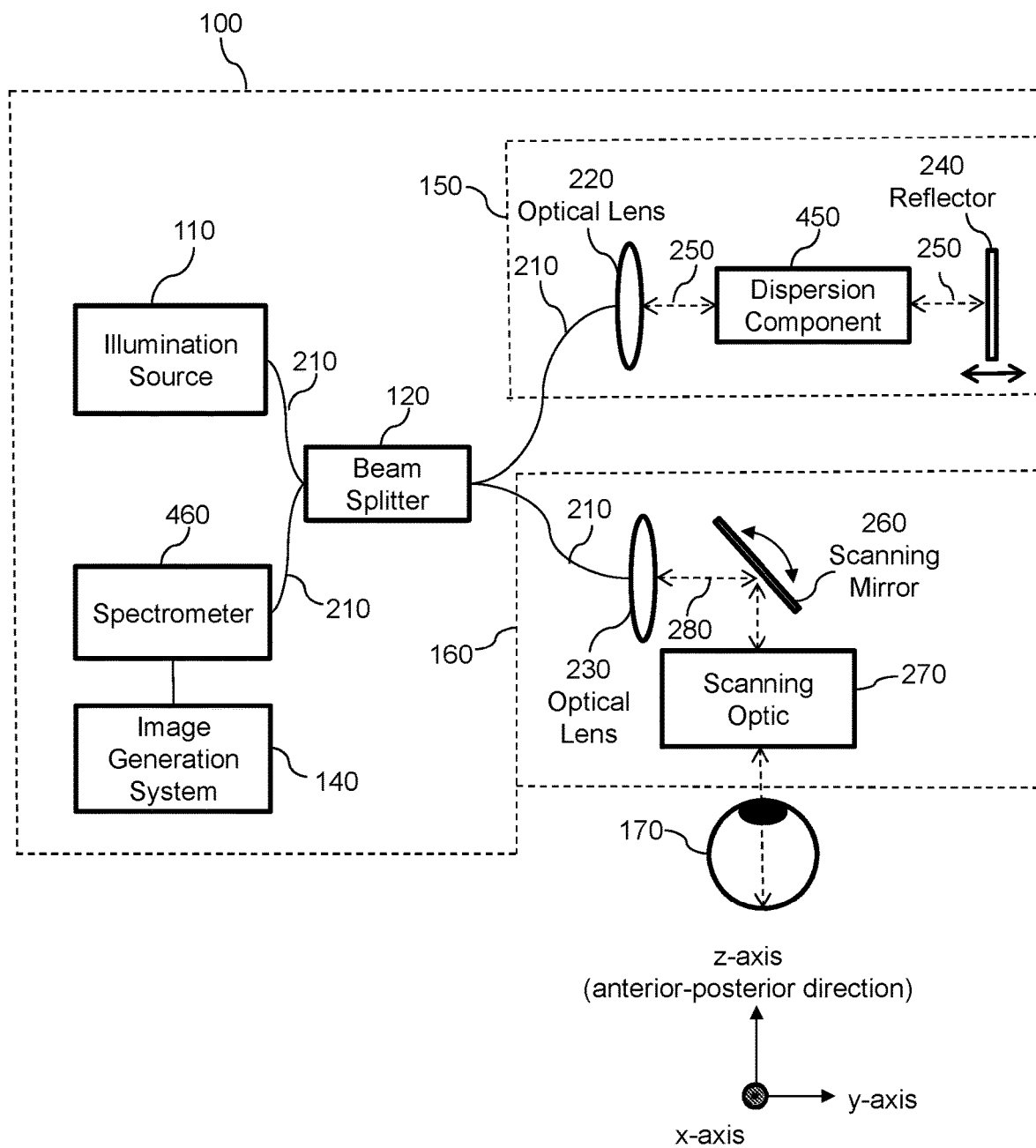
FIG. 3 is schematics of an exemplary generalized SD-OCT system.

An exemplary SD-OCT system is shown in FIG. 3. This exemplary OCT system 100 may comprise at least one illumination source 110, at least one beam splitter 120, at least one spectrometer 460, at least one image generation system 140, at least one reference arm 150, and at least one target arm 160. The reference arm 150 may comprise at least one optical lens 220, at least one dispersion component 450, and at least one reflector 240. The optical lens 220 may be placed between the reflector 240 and the beam splitter 120. The dispersion component 450 may be placed between the reflector 240 and the optical lens 220. The target arm 160 may comprise at least one optical lens 230, at least one scanning mirror 260, and at least one scanning optic 270.

Figure 4:
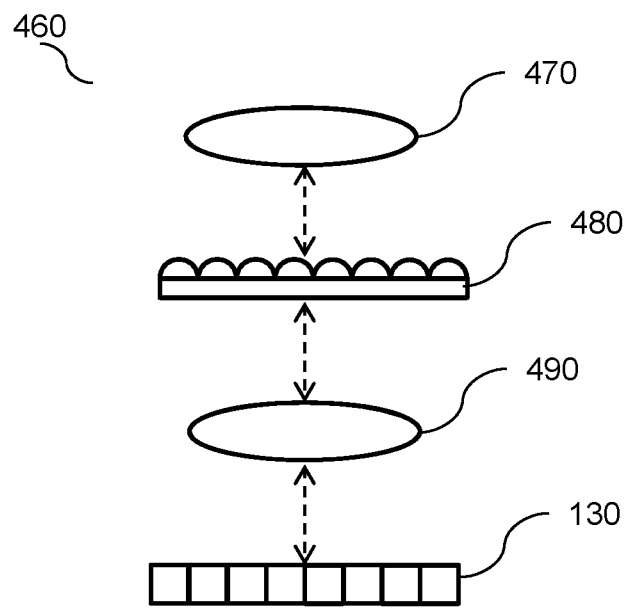
FIG. 4 is schematics of an exemplary generalized spectrometer system for an SD-OCT system.

The spectrometer 460 may comprise at least one first optical lens 470, at least one optical grating 480, at least one second optical lens 490, and at least one detector 130, as shown in FIG. 4. The first optical lens 470 may be placed between the beam splitter 120 and the optical grating 480. The second optical lens 490 may be placed between the optical grating 480 and the detector 130. The first optical lens 470, the optical grating 480, and the second optical lens 490 may be used to project the collected light guided through the beam splitter 120 to the detector 130. The first optical lens 470 may collimate the collected light to the optical grating 480. The optical grating 480 may disperse the collected light into light beams each having a different wavelength. The second optical lens 490 may focus these light beams on different pixels of the detector 130.

Figure 5:
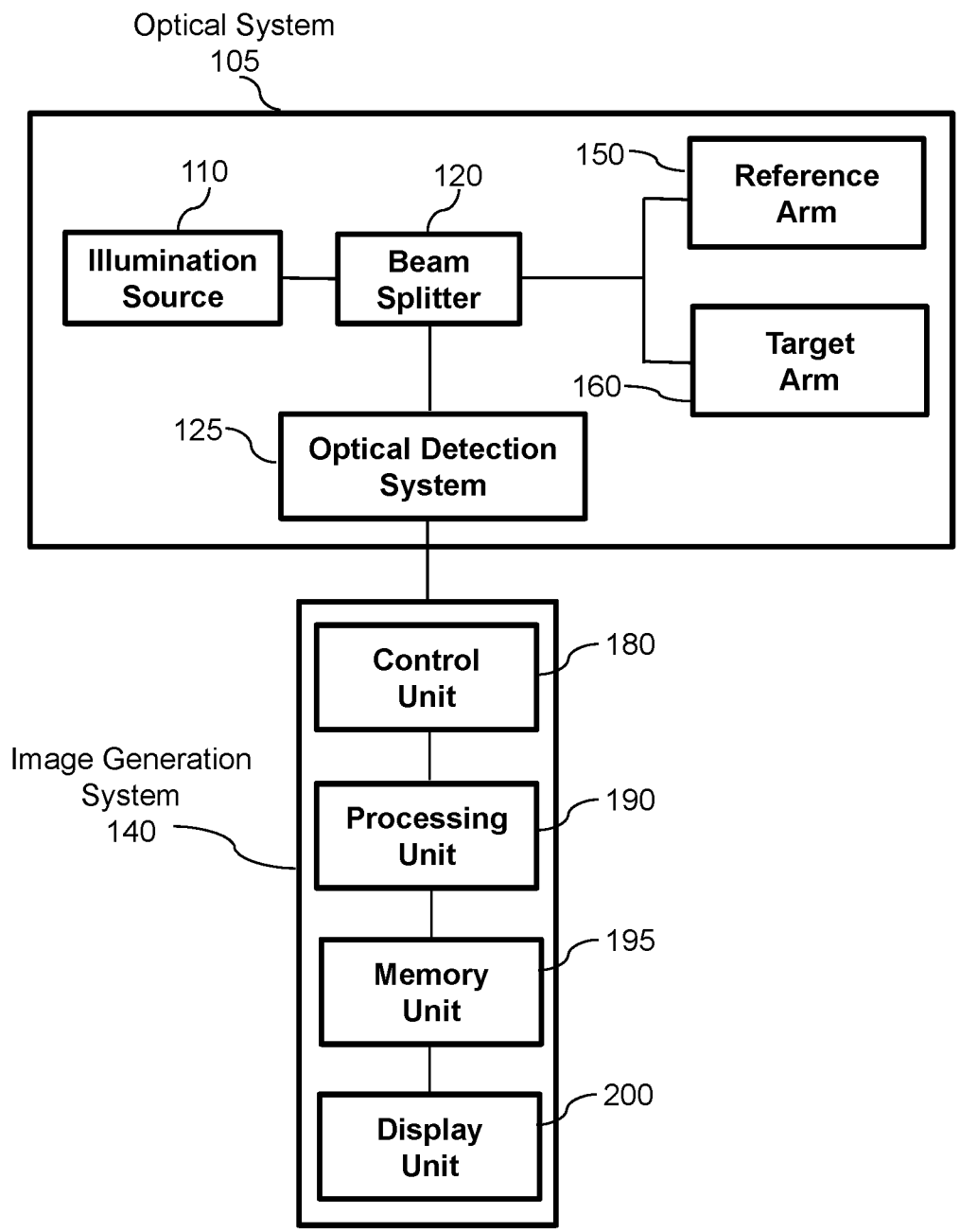
FIG. 5 is schematics of an exemplary generalized image generation system.

The output from the optical system 105 may be supplied to the image generation system 140, as shown in FIG. 5. An exemplary image generation system 140 may comprise at least one control unit 180, at least one processing unit 190, at least one memory unit 195, and a display unit 190. The control unit 180 may be any control system. For example, the control unit may be configured to control the optical system. For example, the control system may be configured to control at least one optical component of the optical system. For example, during the generation of the improved B-scan image, the control unit may control the illumination source, the beam splitter, the reference arm, the target arm, the optical detection system (or the spectrometer), the processing unit, the display unit, or a combination of such unit/system components. The processing unit 190 may be any processing unit. For example, the processing unit may be configured to shape each raw individual B-scan. Results, including the OCT interference spectra, shaped or raw A-scans, shaped or raw B-scans, intensities, processed B-scans, improved B-scans and the like, may be stored in the memory unit 195 or displayed on the display unit 200. The processing and storing functions may be localized within the OCT system or functions may be performed on an external processing unit to which the collected data is transferred. This external unit may be dedicated to data processing or perform other tasks that are quite general and not dedicated to the OCT system.

Figure 6:
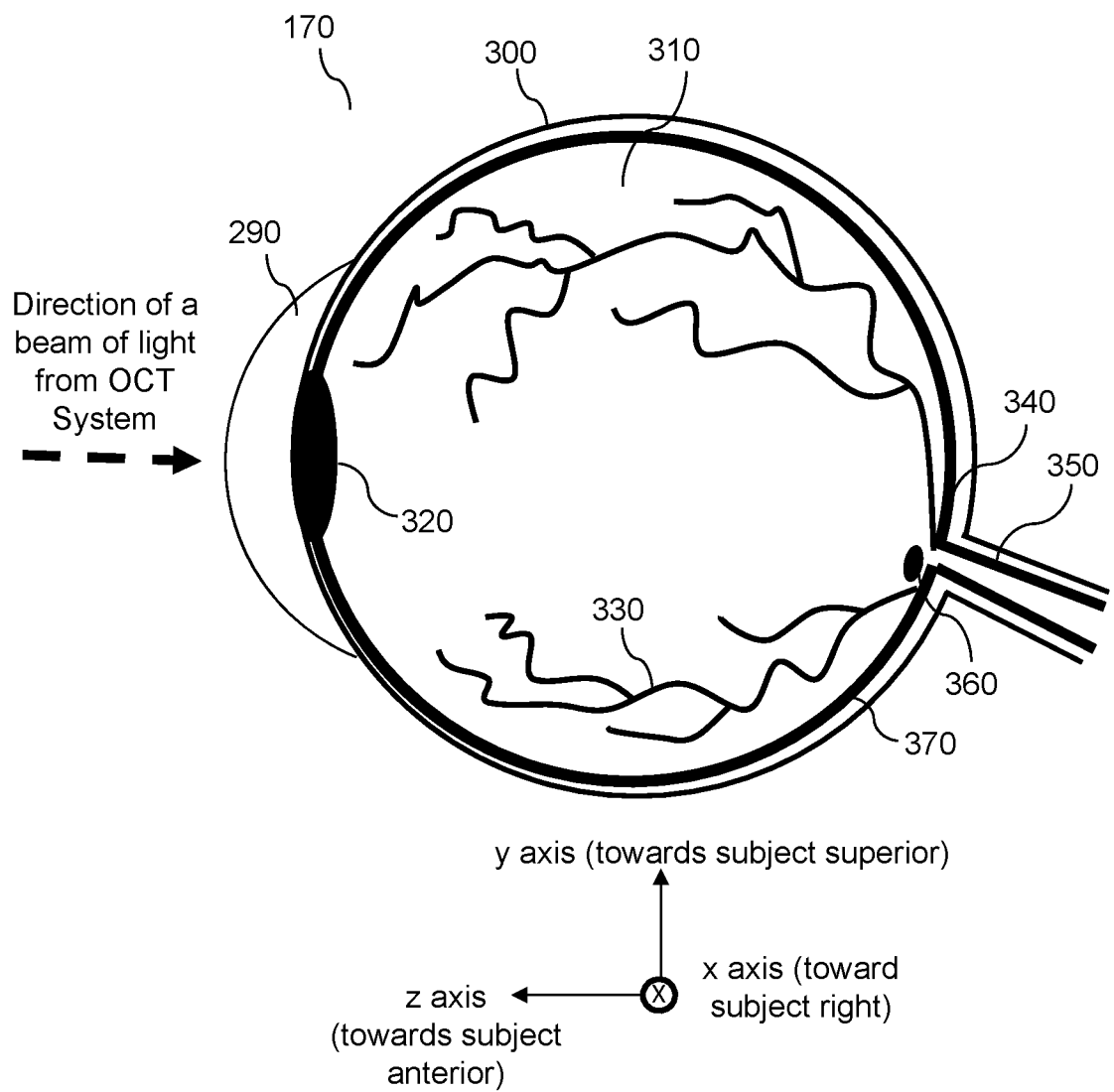
FIG. 6 schematically illustrates sagittal view of a left human eye.

In this disclosure, the target 170 may include any physical object. The physical object has a surface and a depth. For example, the physical object may be an organic tissue. For example, the target may be a human eye, as shown in a simplified manner in FIG. 6. The human eye comprises a cornea 290, a choroid 300, a vitreous chamber 310, a pupil 320, retinal blood vessels 330, a fovea region 340, an optic nerve 350, a retina 370, and an optic disk 360. For example, the target may be any tissue of a human eye. For example, the target may include a retina. For example, the target may include a fundus of an eye. The fundus of an eye has an outer surface receiving light from outside environment through pupil. The fundus of an eye also has a depth starting at and extending from its outer surface.

Figure 7:
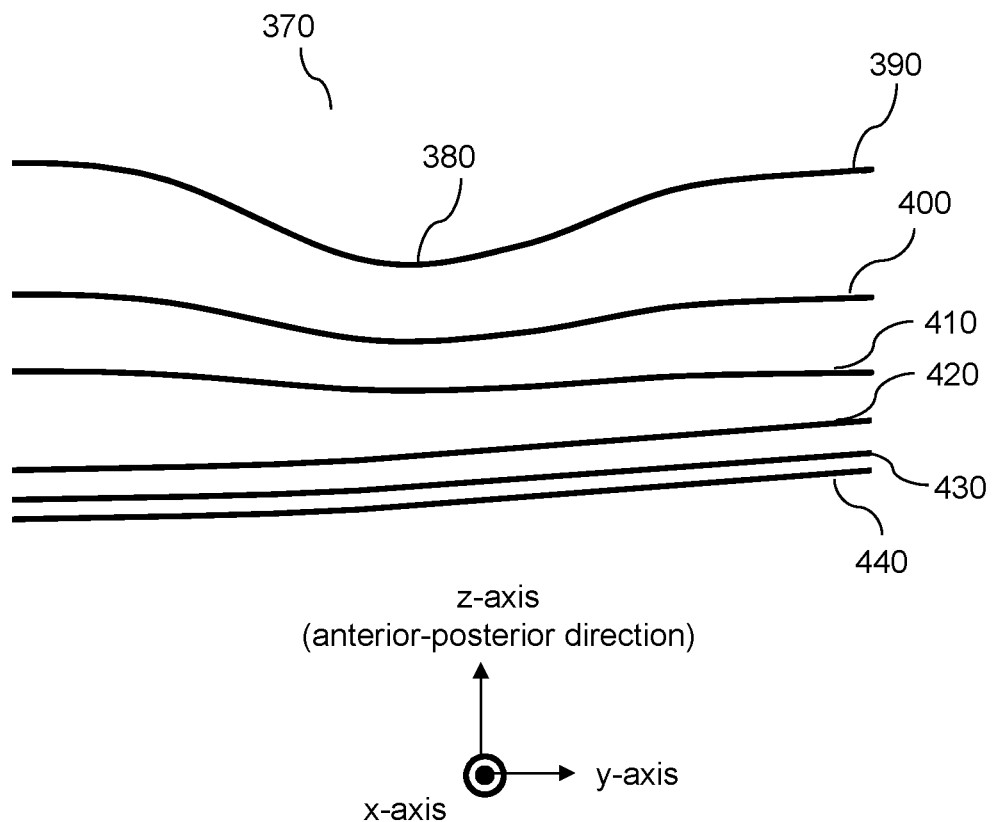
FIG. 7 schematically illustrates cross sectional layers of a retina.

A simplified cross-sectional image of layers of a retina 370 is schematically shown in FIG. 7. The retinal layers comprise a Nerve Fiber Layer (NFL) 390, an External Limiting Membrane (ELM) 400, an Inner/Outer Photoreceptor Segment 410, an Outer Photoreceptor Segment 420, a Retinal Pigment Epithelium (RPE) 430, and a Retinal Pigment Epithelium (RPE)/Bruch's Membrane Complex 440. FIG. 7 also schematically shows the fovea 380. Exemplary cross-sectional OCT images (i.e. B-scans) of the fovea region of the retina are shown FIG. 19.

In this disclosure, a z-axis is an axis parallel to the beam of light extending into the depth of the physical object ("axial axis"), the x-axis and the y-axis ("transverse axes") are transverse, thereby perpendicular axes to the z-axis. Orientation of these three axes in relation to an eye or a retina is shown in FIGS. 1-3, 6-8, and 19-23.

The interference may cause the intensity of the interfered light to vary across the spectrum. The Fourier transform of the interference light may reveal the profile of scattering intensities at different path lengths, and therefore scattering as a function of depth (z-axis direction) in the target (i.e. physical object). See for example Leitgeb et al. "Ultrahigh resolution Fourier domain optical coherence tomography," Optics Express 12(10):2156, 2004. The entire content of this publication is incorporated herein by reference.

Figure 8:
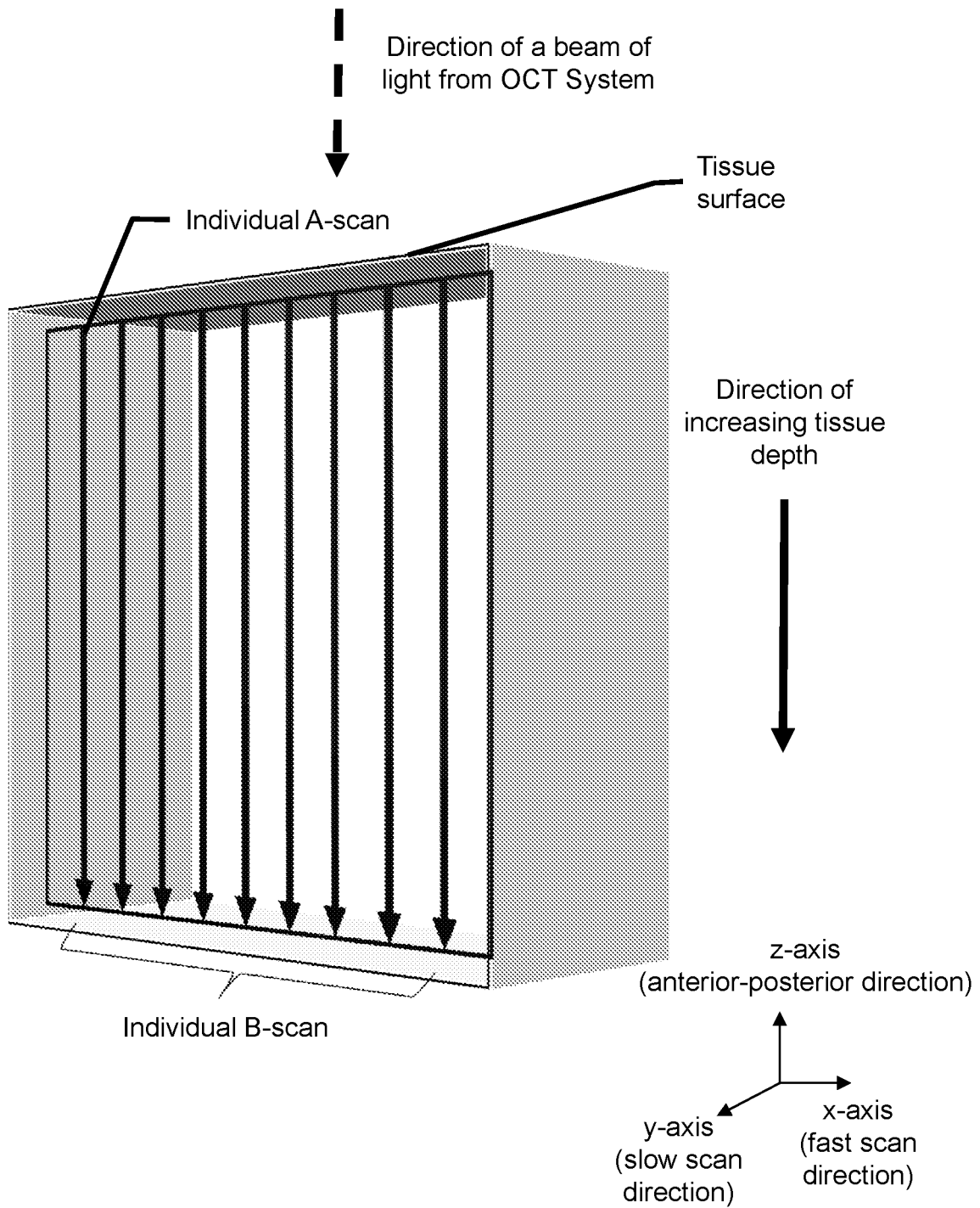
FIG. 8 schematically illustrates A-scans and a B-scan.

The profile of scattering as a function of depth is called an axial scan (A-scan), as schematically shown in FIG. 8. A set of A-scans measured at neighboring locations in the physical object produces a cross-sectional image (tomogram or B-scan) of the physical object. A collection of individual B-scans collected at different transverse locations on the sample makes up a data volume or cube. Three-dimensional C-scans can be formed by combining a plurality of B-scans. For a particular volume of data, the term fast axis refers to the scan direction along a single B-scan whereas slow axis refers to the axis along which multiple B-scans are collected.

In this disclosure, B-scans may be formed by any transverse scanning in the plane designated by the x-axis and y-axis. B-scans may be formed, for example, along the horizontal or x-axis direction, along the vertical or y-axis direction, along the diagonal of x-axis and y-axis directions, in a circular or spiral pattern, and combinations thereof. The majority of the examples discussed herein may refer to B-scans in the x-z axis directions but this disclosure may apply equally to any cross-sectional image.

Figure 9:
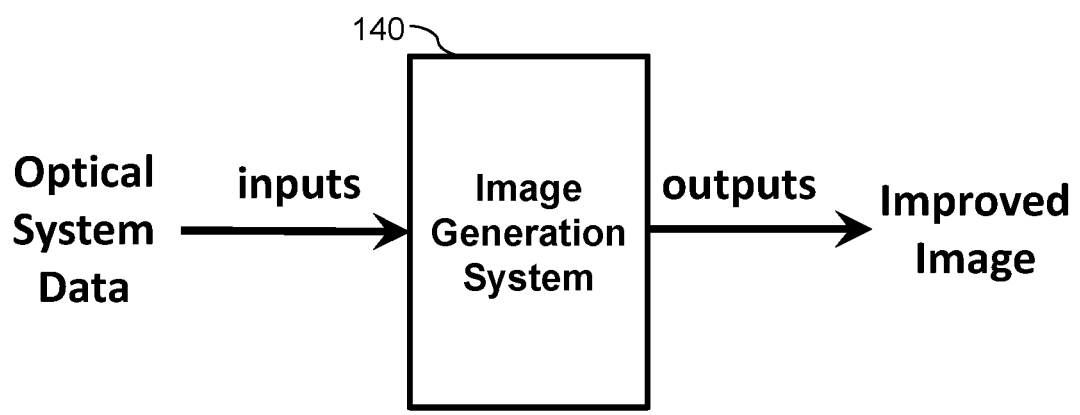
FIG. 9 shows an exemplary image generation system that may receive the detector data as an input and generate an improved OCT image as an output.

In this disclosure, the optical detection system 125 may provide OCT data to the image generation system 140 as an input, and the image generation system may form an improved image (i.e. B-scan) as an output, as shown in FIG. 9.

In this disclosure, the OCT system may have a configuration that illuminates and scans the target.

In this disclosure, the OCT system may have a configuration that forms discretized OCT interference spectra.

In this disclosure, the OCT system may have a configuration that acquires discretized OCT interference spectra. For example, the OCT system may have a configuration that acquires discretized OCT interference spectra from an external system not belonging to the OCT system. The discretized OCT interference spectra, which is acquired, may be in any form, including data, image, the like, or a combination thereof. The external system may be any external system, including another OCT system, a data storage device (e.g. memory disk, hard disk drive, or the like), a computer, the like, or a combination thereof.

In this disclosure, the discretized OCT interference spectra may be formed/acquired in any form. For example, the discretized OCT interference spectra may have a visual form and/or a digital form. For example, the formed/acquired discretized OCT interference spectra may be a stored data. For example, the formed/acquired discretized OCT interference spectra may be stored in the memory unit as data. For example, the formed/acquired discretized OCT interference spectra may be displayed on the image forming system's display. For example, the formed/acquired discretized OCT interference spectra may be an image printed on a paper or any similar media.

In this disclosure, each (raw or shaped) B-scan may comprise at least one (raw or shaped) A-scan. In this disclosure, each (raw or shaped) B-scan may comprise at least two (raw or shaped) A-scans.

In this disclosure, the OCT system may have a configuration that generates raw A-scan and/or raw B-scan from the illumination and the scan. For example, the OCT system may have a configuration that generates at least two raw individual A-scans and/or at least two raw individual B-scans from the illumination and the scan. Each raw individual B-scan may comprise at least one raw individual A-scan. Each raw individual B-scan may comprise at least two raw individual A-scans.

In this disclosure, the OCT system may have a configuration that acquires raw A-scan and/or raw B-scan. For example, the OCT system may have a configuration that acquires at least two raw individual A-scans and/or at least two raw individual B-scans. Each raw individual B-scan may comprise at least one raw individual A-scan. Each raw individual B-scan may comprise at least two raw individual A-scans. For example, the OCT system may have a configuration that acquires raw A-scan and/or raw B-scan from an external system not belonging to the OCT system. The raw A-scan and/or raw B-scan, which is acquired, may be in any form, including data, image, the like, or a combination thereof. The external system may be any external system, including another OCT system, a data storage device (e.g. memory disk, hard disk drive, or the like), a computer, the like, or a combination thereof.

In this disclosure, the raw A-scan and/or raw B-scan may be generated/acquired in any form. For example, the raw A-scan and/or raw B-scan may have a visual form and/or a digital form. For example, the generated/acquired raw A-scan and/or raw B-scan may be a stored data. For example, the generated/acquired raw A-scan and/or raw B-scan may be stored in the memory unit as data. For example, the generated/acquired raw A-scan and/or raw B-scan may be displayed on the image generation system's display unit. For example, the generated/acquired raw A-scan and/or raw B-scan may be an image printed on a paper or any similar media.

In this disclosure, the OCT system may have a configuration that shapes each raw A-scan by using at least two different shaping functions for each raw A-scan to form at least two shaped A-scans for each raw A-scan.

In this disclosure, the OCT system may have a configuration that forms at least two B-scans ("shaped B-scan"). The shaped A-scans forming the same shaped B-scan may be shaped with the same shaping function.

In this disclosure, the OCT system may have a configuration that acquires at least two shaped B-scans. Each shaped B-scan may comprise at least two shaped A-scans. The at least two shaped A-scans forming the same B-scan may be shaped with the same shaping function. For example, the OCT system may have a configuration that acquires at least two shaped B-scans from an external system not belonging to the OCT system. The at least two shaped B-scans, which is acquired, may be in any form, including data, image, the like, or a combination thereof. The external system may be any external system, including another OCT system, a data storage device (e.g. memory disk, hard disk drive, or the like), a computer, the like, or a combination thereof.

In this disclosure, the at least two shaped B-scans may be generated/acquired in any form. For example, the at least two shaped B-scans may have a visual form and/or a digital form. For example, the generated/acquired at least two shaped B-scans may be a stored data. For example, the generated/acquired at least two shaped B-scans may be stored in the memory unit as data. For example, the at least two shaped B-scans may be displayed on the image generation system's display unit. For example, the generated/acquired at least two shaped B-scans may be an image printed on a paper or any similar media.

In this disclosure, the OCT system may have a configuration that generates a shaped B-scan cluster comprising at least two shaped B-scans.

In this disclosure, the OCT system may have a configuration that acquires a shaped B-scan cluster comprising at least two shaped B-scans. For example, the OCT system may have a configuration that acquires a shaped B-scan cluster from an external system not belonging to the OCT system. The shaped B-scan cluster, which is acquired, may be in any form, including data, image, the like, or a combination thereof. The external system may be any external system, including another OCT system, a data storage device (e.g. memory disk, hard disk drive, or the like), a computer, the like, or a combination thereof.

In this disclosure, the shaped B-scan cluster may be generated/acquired in any form. For example, the shaped B-scan cluster may have a visual form and/or a digital form. For example, the generated/acquired shaped B-scan cluster may be a stored data. For example, the generated/acquired shaped B-scan cluster may be stored in the memory unit as data. For example, the generated/acquired shaped B-scan cluster may be displayed on the image generation system's display unit. For example, the generated/acquired shaped B-scan cluster may be an image printed on a paper or any similar media.

In this disclosure, the OCT system may have a configuration that determines a maximum intensity of each shaped B-scan.

In this disclosure, the OCT system may have a configuration that normalizes each shaped B-scan ("normalized B-scan") by using the maximum intensity of the same shaped B-scan.

In this disclosure, the OCT system may have a configuration that selects one pixel for each normalized shaped B-scan ("B-scan pixel").

In this disclosure, the OCT system may have a configuration that processes intensity values of selected B-scan pixels of all normalized shaped B-scans by using a mathematical operation, wherein the selected B-scan pixels have the same position on all normalized shaped B-scans, and wherein the all normalized shaped B-scan belong to the same multi-shaped B-scan image cluster.

In this disclosure, the OCT system may have a configuration that stores the processed intensity values in a two-dimensional array. The processed intensity values may be stored in any form. They may be stored as data, image, the like, or a combination thereof. They may be stored by using devices/systems including the OCT system's memory unit, an external data storage device (e.g. memory disk, hard disk drive, or the like), a computer, the like, or a combination thereof.

In this disclosure, the OCT system may have a configuration that repeats the processing and the storing of intensity values for all B-scan pixels of all normalized shaped B-scans.

In this disclosure, the OCT system may have a configuration that forms sets of pixels. Each pixel set may comprise one pixel ("B-scan pixel") from each normalized B-scan. The B-scan pixels of each pixel set may have the same position on all normalized B-scans.

In this disclosure, the OCT system may have a configuration that generates a processed B-scan based on this two-dimensional array.

In this disclosure, the processed B-scan may be generated in any form. For example, the processed B-scan may have a visual form and/or a digital form. For example, the processed B-scan image may be a stored data. For example, the processed B-scan image may be stored in the memory unit as data. For example, the processed B-scan image data may be displayed on the image generation system's display unit.

For example, the processed B-scan image may be an image printed on a paper or any similar media.

In this disclosure, the OCT system may have a configuration that determines one intensity ("optimized intensity") for each pixel set by applying a mathematical operation to intensities of pixels forming the same pixel set. The mathematical operation may comprise a rank order filter, a mean filter, a multi-image deconvolution, or a combination thereof.

In this disclosure, the OCT system may have a configuration that generates a new B-scan ("new B-scan") based on the optimized intensities of the pixel sets. The new B-scan may be a B-scan that has an improved image quality over a raw B-scan that may be formed only from (raw) A-scans. The new B-scan may be a B-scan that has an improved image quality over a B-scan that may be formed without shaping (raw) A-scans.

In this disclosure, the improved B-scan image may be generated in any form. For example, the improved B-scan image may have a visual form and/or a digital form. For example, the improved B-scan image may be a stored data. For example, the improved B-scan image may be stored in the memory unit as data. For example, the improved B-scan image may be displayed on the image generation system's display unit. For example, the improved B-scan image may be an image printed on a paper or any similar media.

In this disclosure, the OCT system may have a configuration that displays the improved B-scan image on the image generation system's display.

The OCT system of this disclosure may provide improved OCT (i.e. B-scan) images of a target 170 by reducing the axial sidelobe noise without the price of hindering the axial resolution. The improved image of the target 170 may be generated by processing the interference (i.e. OCT) spectra of multiple shapes. In one example, the improved image may be generated by the image generation system 140 that uses these multiple shaping functions ("multi-shaping technique"). In another example, the improved image may be generated by controlling pixels of the optical detection system 125 that acquires the data ("detector multi-apodization technique").

Figure 10:
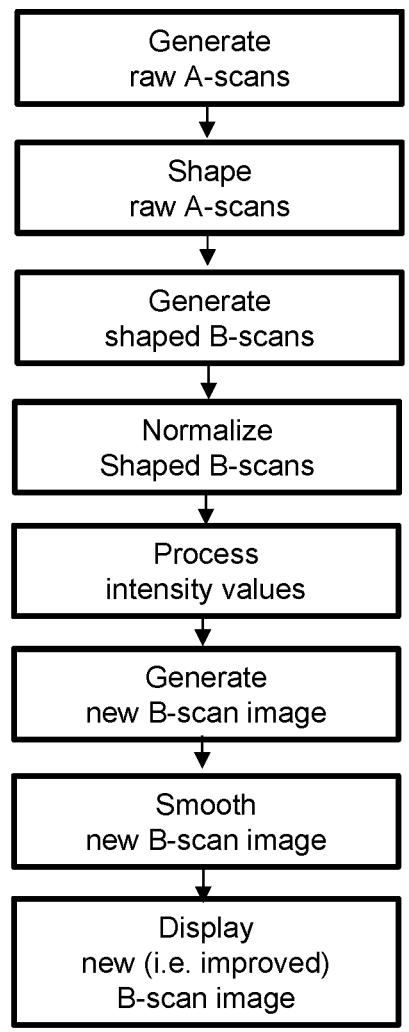
FIG. 10 schematically shows an exemplary multi-shaping technique used by the image generation system to generate an improved B-scan image from the acquired raw B-scan.

An exemplary multi-shaping technique is schematically demonstrated in FIG. 10. In this example, an optical coherence tomography (OCT) system 100 may scan a target 170 that has a surface and a depth by using the illumination source 110. Then, it may form discretized OCT interference spectra from the scan by using the detector 130, thereby generating raw A-scans from the scan.

Figure 11:
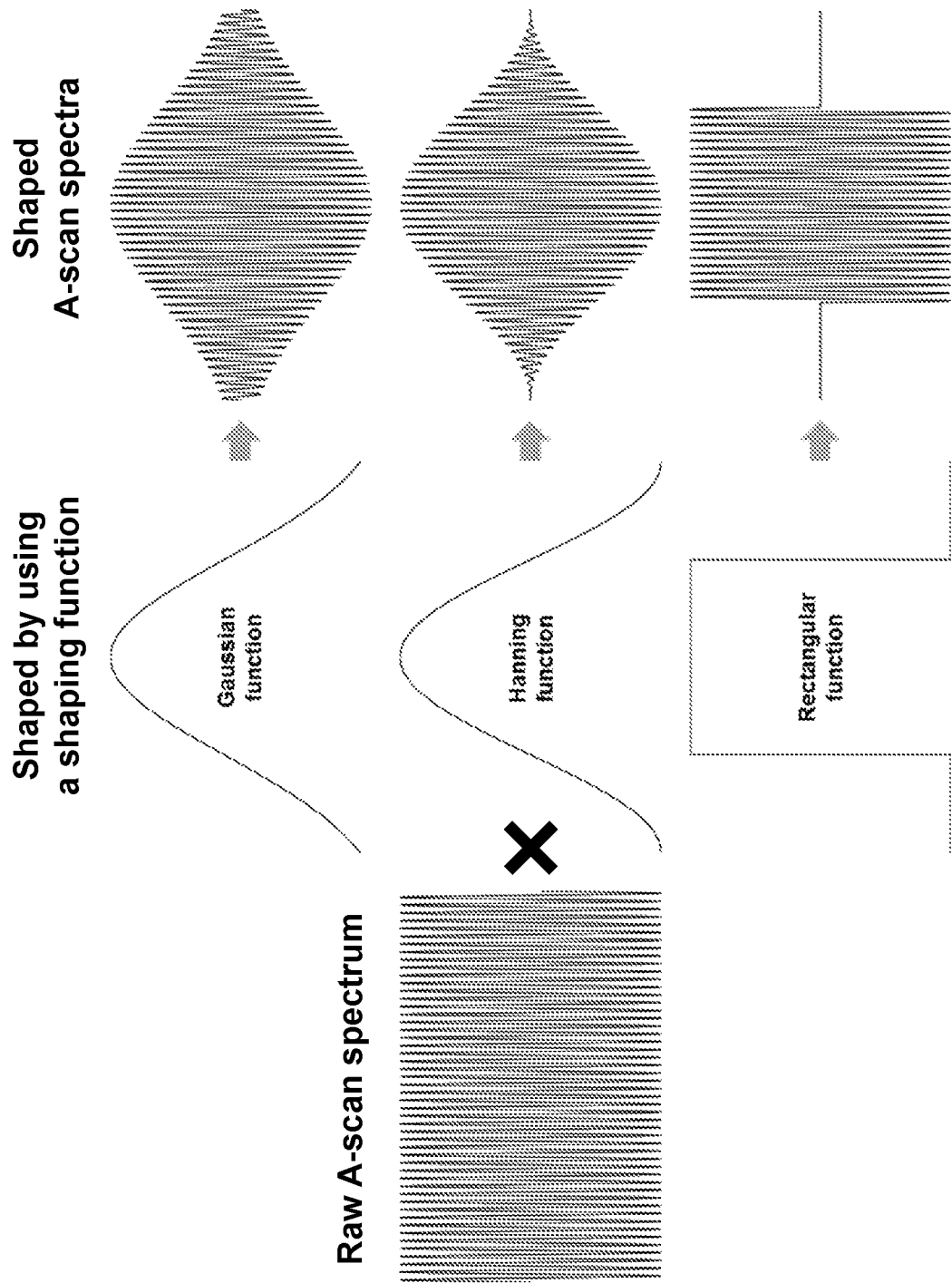
FIG. 11 shows shaping of a raw A-scan by using a shaping function. Three different shaping function examples, shown in this figure, include a Gaussian function, a Hanning Function, and a rectangular function.

These raw A scans are then shaped by using shaping functions. The shaping function may be any shaping function suitable for shaping the raw B-scan. The shaping (e.g. window) function may be a function that is zero-valued outside of some chosen (i.e. predetermined) interval. For example, a shaping function that is constant inside the interval and zero elsewhere is called a rectangular window, where its graphical shape is a rectangle. Examples of the shaping functions may be functions of "bell-shaped" curves, rectangles, triangles, the like, or a combination thereof. Examples of the shaping functions may be a Gaussian function, a Hamming function, a Hanning function, or a combination thereof. Such functions are schematically shown in FIG. 11. The image generation system multiplies a raw A-scan spectrum with a shaping function to generate a shaped A-scan spectrum.

In this disclosure, the OCT system may shape each raw A-scan by using at least two different shaping functions, wherein the shaping forms at least two shaped A-scans.

Figure 12:
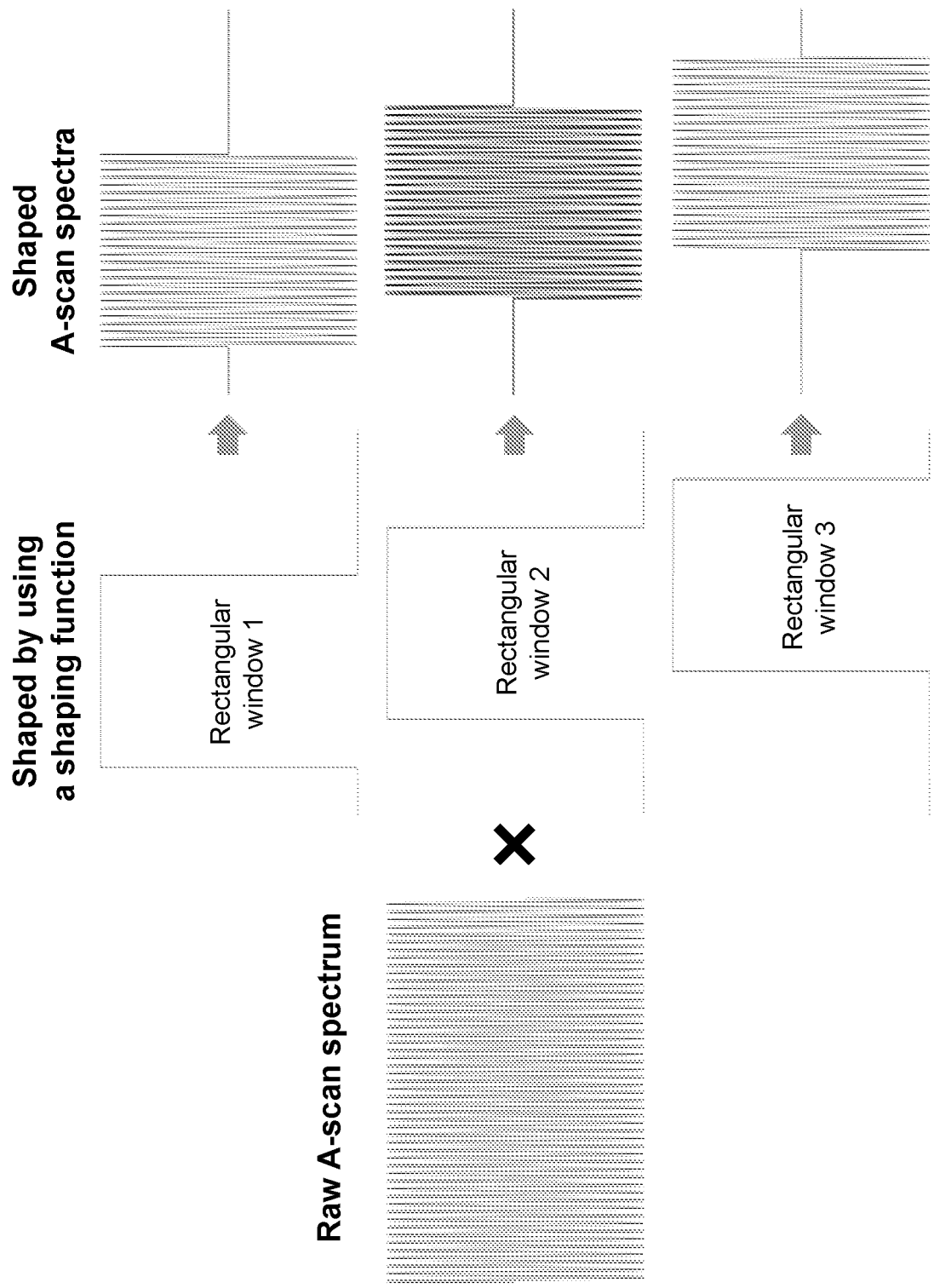
FIG. 12 shows shaping of a raw A-scan by using a rectangular shaping function. Rectangular windows in three rectangular function examples have same size, but different central positions.
Figure 13:
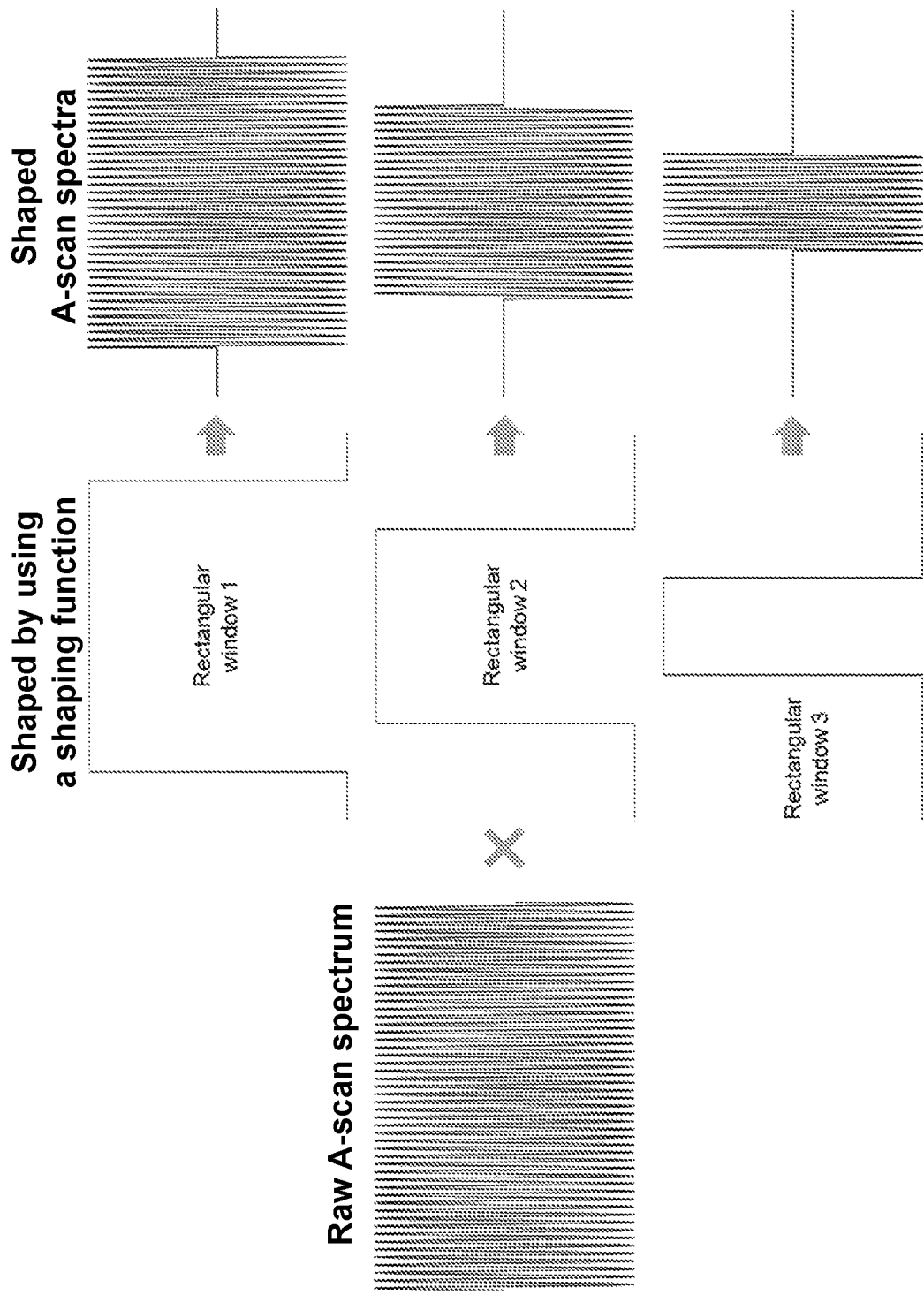
FIG. 13 shows shaping of a raw A-scan by using a rectangular shaping function. Rectangular windows in three rectangular function examples have same central position, but have different sizes.

In one example, the different shaping functions may be rectangular functions that have same rectangular sizes, but have rectangular windows at different central locations, as shown in FIG. 12. In another example, the different shaping functions may be rectangular functions that have different rectangular sizes, but have rectangular windows with same central location, as shown in FIG. 13.

In this disclosure, the shaped B-scan may be generated from at least one shaped A-scan. In this disclosure, the shaped B-scan may be generated from at least two shaped A-scans.

Then, in one example, the OCT system may, for example, normalize each B-scan image to a maximum intensity of same B-scan image as follows. Each B-scan image may comprise at least one pixel. The image generation system may select one pixel for each B-scan image, and it then may process intensity values of selected pixels of all B-scan images by using a mathematical operation. The mathematical operation may be any mathematical operation. The mathematical operation may be a rank order filter, a mean filter, a multi-image deconvolution, or a combination thereof. Examples of the rank order filter may be a minimum filter, a median filter, a rank order filter that may have a rank between that of the minimum filter and the median filter, the like, or a combination thereof. For example, the rank order filter's rank may be $17^{th}$ smallest value. Examples of the mean calculation may be an arithmetic mean, a weighted mean, a geometric mean, a harmonic mean, a quadratic mean, a logarithmic mean, the like, or a combination thereof. Exemplary multi-image deconvolution techniques may be disclosed in: Yaroslaysky et al. "Deconvolution of multiple images of the same object" Applied Optics, Volume 33, Issue 11, April 1994, Pages 2157-2162; Castello et al. "Multi-images deconvolution improves signal-to-noise ratio on gated stimulated emission depletion microscopy" Applied Physics Letter, Volume 105, December 2014, Pages 234106; Park et al. "Gyro-based multi-image deconvolution for removing handshake blur" CVPR, June 2014. All these publications are incorporated herein by reference in their entirety.

Figure 14:
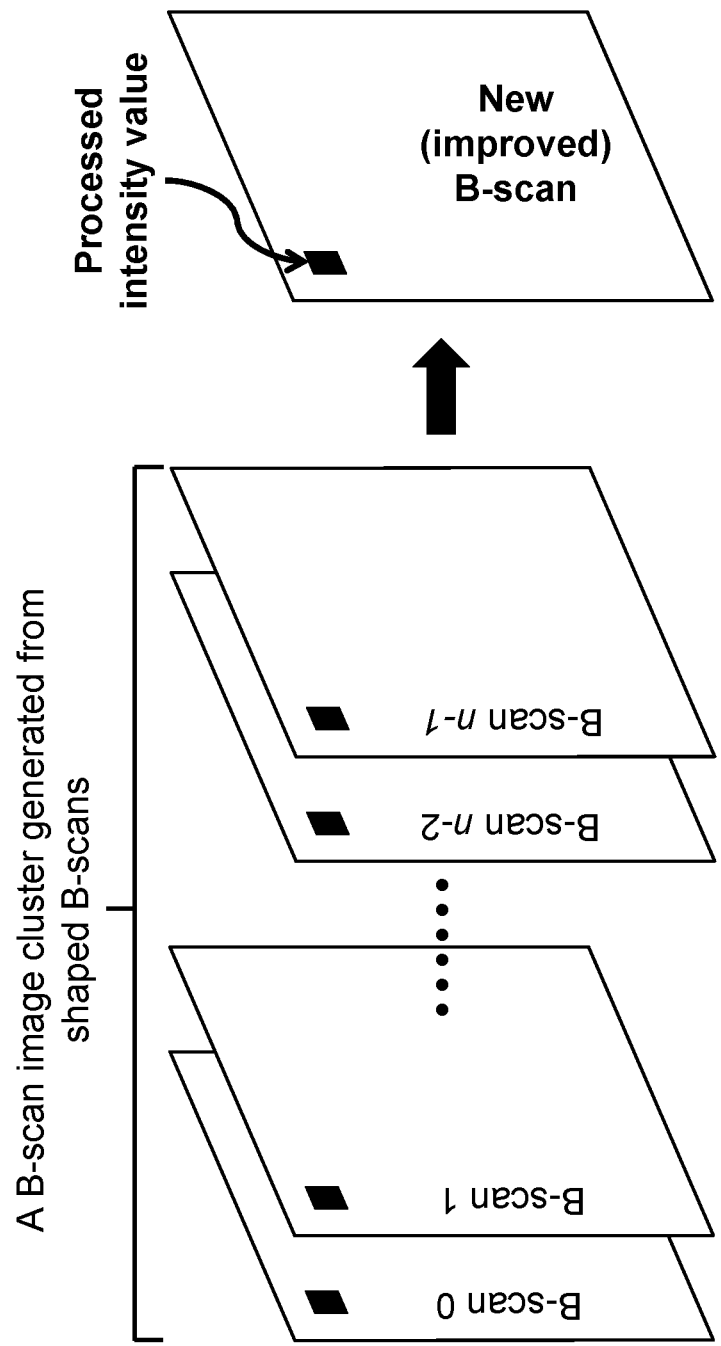
FIG. 14 shows intensity value processing on a B-scan image cluster.

Then, in one example, the OCT system may generate a processed intensity value. The selected pixels may have a same position on all B-scan images. The all B-scan images may belong to same B-scan image cluster. The system may store the processed intensity value in a two-dimensional array, repeat the intensity value processing and storing for all pixels, and generate a new (processed) B-scan image from this two-dimensional array. This intensity value processing process is schematically shown in FIG. 14.

Then, in one example, the OCT system may smooth the new (processed) B-scan image by using a digital filter. The digital filter may be any digital filter. For example, the digital filter may comprise a smoothing filter. Examples of the smoothing filter may comprise a linear smoothing filter, a non-linear smoothing filter, the like, or a combination thereof. For example, the smoothing filter may comprise a median filter, a Gaussian filter, the like, or a combination thereof.

The OCT system may thereby generate an improved B-scan image. Finally, in one example, the OCT may display an improved B-scan image.

In this disclosure, the OCT system may generate improved B-scan images for all raw B-scan data.

Figure 15:
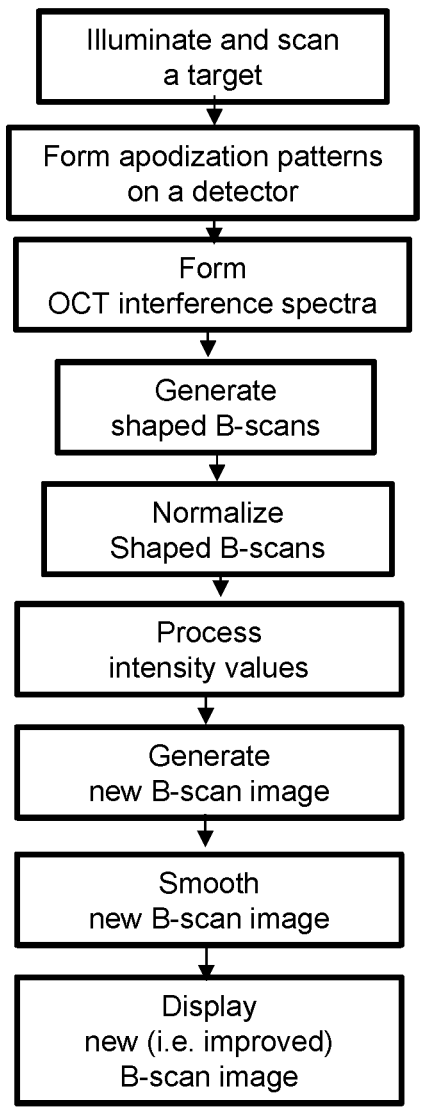
FIG. 15 schematically shows an exemplary detector multi-apodization technique used by an SD-OCT system to generate an improved B-scan image from an acquired/generated raw B-scan cluster.
Figure 16:
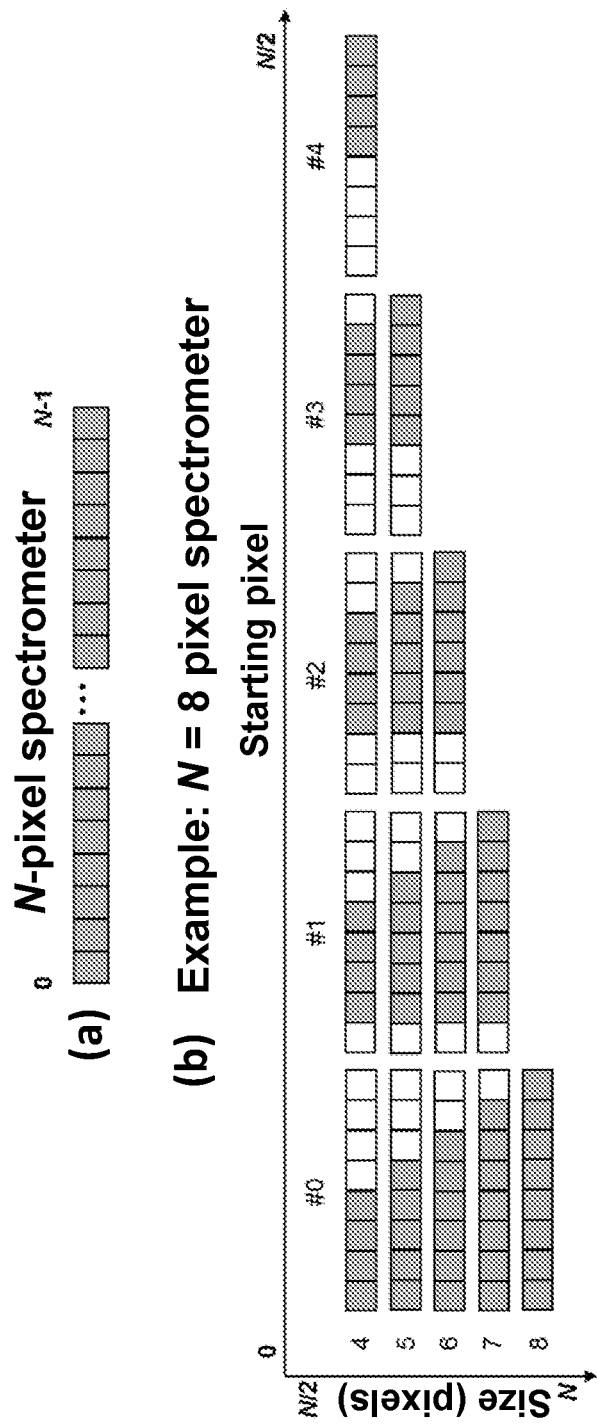
FIG. 16 schematically shows an exemplary apodization pattern generation on an exemplary detector, (a) in one example, the exemplary detector may have N pixels, (b) in another example, the exemplary detector may have 8 pixels with which 15 apodization patterns may be created.

An exemplary detector multi-apodization technique is schematically demonstrated in FIG. 15. In this example, the OCT system may comprise any OCT system. For example, the OCT system's components may form a spectral domain optical coherence tomography (SD-OCT) system. The OCT system may comprise an illumination source 110, a beam splitter 120, a reference arm 150, a target arm 160, a spectrometer 460, and an image generation system 140. The spectrometer may comprise an optical grating 480, a detector 130, a first optical lens 470 placed between the beam splitter 120 and the optical grating 480, and a second optical lens 490 placed between the optical grating 480 and the detector 130. The detector 130 may comprise at least three pixels. The first optical lens 470, the optical grating 480 and the second optical lens 490 may project interfered light beam formed after the beam splitter 120 on the at least three pixels.

In this disclosure, the optical system may comprise an illumination source, a beam splitter, a reference arm, a target arm, and an optical detection system comprising a spectrometer. The spectrometer may comprise a detector. The detector may comprise at least three pixels ("detector pixels"). An example of such detector may be a pixel detector. Complementary metal-oxide-semiconductor (CMOS) image sensor may be an example of a pixel detector. The spectrometer may further comprise an optical grating, a first optical lens placed between the beam splitter and the grating, and a second optical lens placed between the optical grating and the detector. The first lens, the grating and the second lens may have a configuration that projects interfered light beam formed by the beam splitter on the at least three detector pixels.

In this disclosure, the OCT system may have a configuration that illuminates and scans at least one physical position on a target's surface.

In this disclosure, the OCT system may have a configuration that forms sets of detector pixels. Each detector pixel set may comprise at least one detector pixel. Each detector pixel set may comprise at least two detector pixels. The detector pixels forming the same detector pixel set may be adjacent to each other. Apodization patterns may thereby formed.

In this disclosure, the OCT system may have a configuration that forms discretized OCT interference spectra on each detector pixel.

In this disclosure, the OCT system may have a configuration that generates/acquire at least two (raw) A-scans. Each (raw) A-scan may be generated/acquired from the discretized OCT interference spectra formed on each detector pixel.

For example, the OCT system may have a configuration that acquires raw A-scan from an external system not belonging to the OCT system. The raw A-scan, which is acquired, may be in any form, including data, image, the like, or a combination thereof. The external system may be any external system, including another OCT system, a data storage device (e.g. memory disk, hard disk drive, or the like), a computer, the like, or a combination thereof.

In this disclosure, the raw A-scan may be generated/ acquired in any form. For example, the raw A-scan data and/or raw B-scan data may have a visual form and/or a digital form. For example, the generated/acquired raw A-scan may be a stored data. For example, the generated/ acquired raw A-scan may be stored in the memory unit as data. For example, the generated/acquired raw A-scan may be displayed on the image generation system's display unit. For example, the generated/acquired raw A-scan may be an image printed on a paper or any similar media.

In this disclosure, the OCT system may have a configuration that forms/acquires at least two B-scans ("shaped B-scan") based on the generated/acquired A-scans. The A-scans forming each shaped B-scan may be generated from the discretized OCT interference spectra formed on the detector pixels of the same detector pixel set.

In this disclosure, the OCT system may have any combination of above configurations.

For example, the OCT system for generating a B-scan image of a target that has a surface and a depth may comprise an optical system and an image generation system. The optical system may comprise an illumination source, a beam splitter, a target arm, a reference arm, and an optical detection system, or a combination thereof. The image generation system may comprise a control unit, a processing unit, a memory unit, a display unit, or a combination thereof. The OCT system may have a configuration that, during operation, may illuminate and scan the target; may form discretized OCT interference spectra; may generate at least two raw A-scans; may shape each raw A-scan by using at least two different shaping functions for each raw A-scan to form at least two shaped A-scans for each raw A-scan; may form at least two B-scans ("shaped B-scan"). The shaped A-scans forming the same shaped B-scan may be shaped with the same shaping function. The OCT system may have a configuration that, during operation, may determine a maximum intensity of each shaped B-scan; may normalize each shaped B-scan ("normalized B-scan") by using the maximum intensity of the same shaped B-scan; may form sets of pixels. Each pixel set may comprise one pixel ("B-scan pixel") from each normalized B-scan. The B-scan pixels of each pixel set may have the same position on all normalized B-scans. The OCT system may have a configuration that, during operation, may determine one intensity ("optimized intensity") for each pixel set by applying a mathematical operation to intensities of pixels forming the same pixel set. The mathematical operation may comprise a rank order filter, a mean filter, a multi-image deconvolution, or a combination thereof. The OCT system may have a configuration that, during operation, may generate a new B-scan ("new B-scan") based on the optimized intensities of the pixel sets. The OCT system may have a configuration that, during operation, may display the new B-scan on the image generation system's display unit.

For example, the OCT system for generating a B-scan image of a target that has a surface and a depth may comprise an optical system and an image generation system. The optical system may comprise an illumination source, a beam splitter, a reference arm, a target arm, and an optical detection system comprising a spectrometer. The spectrometer may comprise a detector. The detector may comprise at least three pixels ("detector pixels"). The OCT system may have a configuration that, during operation, may illuminate and scans at least one physical position on the target surface; and may form sets of detector pixels. Each detector pixel set may comprise at least two detector pixels. The detector pixels forming the same detector pixel set may be adjacent to each other. The OCT system may have a configuration that, during operation, may form discretized OCT interference spectra on each detector pixel; and may generate at least two A-scans. Each A-scan may be generated from the discretized OCT interference spectra formed on each detector pixel. The OCT system may have a configuration that, during operation, may form at least two B-scans ("shaped B-scan") based on generated A-scans. The A-scans forming each shaped B-scan may be generated from the discretized OCT interference spectra formed on the detector pixels of the same detector pixel set. The OCT system may have a configuration that, during operation, may determine a maximum intensity of each shaped B-scan; may normalize each shaped B-scan ("normalized B-scan") by using the maximum intensity of the same shaped B-scan; and may form sets of pixels. Each pixel set may comprise one pixel ("B-scan pixel") from each normalized B-scan. The B-scan pixels of each pixel set may have the same position on all normalized B-scans. The OCT system may have a configuration that, during operation, may determine one intensity ("optimized intensity") for each pixel set by applying a mathematical operation to intensities of pixels forming the same pixel set. The mathematical operation may comprise a rank order filter, a mean filter, a multi-image deconvolution, or a combination thereof. The OCT system may have a configuration that, during operation, may generate a new B-scan ("new B-scan") based on the optimized intensities of the pixel sets. The OCT system may have a configuration that, during operation, may display the new B-scan on the image generation system's display unit.

For example, the OCT system for generating a B-scan image of a target that has a surface and a depth, wherein the OCT system may have a configuration that, during operation, may illuminate and scans the target; may form discretized OCT interference spectra; may generate at least two raw A-scans; may shape each raw A-scan by using at least two different shaping functions for each raw A-scan to form at least two shaped A-scans for each raw A-scan; and may form at least two B-scans ("shaped B-scan"). The shaped A-scans forming the same shaped B-scan may be shaped with the same shaping function. The OCT system may have a configuration that, during operation, may determine a maximum intensity of each shaped B-scan; may normalize each shaped B-scan ("normalized B-scan") by using the maximum intensity of the same shaped B-scan; and may form sets of pixels. Each pixel set may comprise one pixel ("B-scan pixel") from each normalized B-scan. The B-scan pixels of each pixel set may have the same position on all normalized B-scans. The OCT system may have a configuration that, during operation, may determine one intensity ("optimized intensity") for each pixel set by applying a mathematical operation to intensities of pixels forming the same pixel set. The mathematical operation may comprise a rank order filter, a mean filter, a multi-image deconvolution, or a combination thereof. The OCT system may have a configuration that, during operation, may generate a new B-scan ("new B-scan") based on the optimized intensities of the pixel sets.

For example, the OCT system for generating a B-scan image of a target that has a surface and a depth, wherein the OCT system may have a configuration that, during operation, may acquire at least two raw A-scans; may shape each raw A-scan by using at least two different shaping functions for each raw A-scan to form at least two shaped A-scans for each raw A-scan; and may form at least two B-scans ("shaped B-scan"). The shaped A-scans forming the same shaped B-scan may be shaped with the same shaping function. The OCT system may have a configuration that, during operation, may determine a maximum intensity of each shaped B-scan; may normalize each shaped B-scan ("normalized B-scan") by using the maximum intensity of the same shaped B-scan; and may form sets of pixels. Each pixel set may comprise one pixel ("B-scan pixel") from each normalized B-scan. The B-scan pixels of each pixel set may have the same position on all normalized B-scans. The OCT system may have a configuration that, during operation, may determine one intensity ("optimized intensity") for each pixel set by applying a mathematical operation to intensities of pixels forming the same pixel set. The mathematical operation may comprise a rank order filter, a mean filter, a multi-image deconvolution, or a combination thereof. The OCT system may have a configuration that, during operation, may generate a new B-scan ("new B-scan") based on the optimized intensities of the pixel sets.

For example, the OCT system for generating a B-scan image of a target that has a surface and a depth, wherein the OCT system may have a configuration that, during operation, may acquire at least two B-scans ("shaped B-scans"). Each shaped B-scan may comprise at least two shaped A-scans. Each shaped A-scan may be formed by shaping a raw A-scan by using at least two different shaping functions. The at least two shaped A-scans forming the same shaped B-scan may be shaped with the same shaping function. The OCT system may have a configuration that, during operation, may determine a maximum intensity of each shaped B-scan; may normalize each shaped B-scan ("normalized B-scan") by using the maximum intensity of the same shaped B-scan; and may form sets of pixels. Each pixel set may comprise one pixel ("B-scan pixel") from each normalized B-scan. The B-scan pixels of each pixel set may have the same position on all normalized B-scans. The OCT system may have a configuration that, during operation, may determine one intensity ("optimized intensity") for each pixel set by applying a mathematical operation to intensities of pixels forming the same pixel set. The mathematical operation may comprise a rank order filter, a mean filter, a multi-image deconvolution, or a combination thereof. The OCT system may have a configuration that, during operation, may generate a new B-scan ("new B-scan") based on the optimized intensities of the pixel sets.

For example, the OCT system for generating a B-scan image of a target that has a surface and a depth, wherein, when the OCT system is incorporated to an image generation system, the OCT system may cause an image generation system to have a configuration that, during operation, may form or acquire at least two B-scans ("shaped B-scans"). Each shaped B-scan may comprise at least two shaped A-scans. Each shaped A-scan may be formed by shaping a raw A-scan by using at least two different shaping functions. The at least two shaped A-scans forming the same shaped B-scan may be shaped with the same shaping function. The OCT system may have a configuration that, during operation, may determine a maximum intensity of each shaped B-scan; may normalize each shaped B-scan ("normalized B-scan") by using the maximum intensity of the same shaped B-scan; and may form sets of pixels. Each pixel set may comprise one pixel ("B-scan pixel") from each normalized B-scan. The B-scan pixels of each pixel set may have the same position on all normalized B-scans. The OCT system may have a configuration that, during operation, may determine one intensity ("optimized intensity") for each pixel set by applying a mathematical operation to intensities of pixels forming the same pixel set. The mathematical operation may comprise a rank order filter, a mean filter, a multi-image deconvolution, or a combination thereof. The OCT system may have a configuration that, during operation, may generate a new B-scan ("new B-scan") based on the optimized intensities of the pixel sets.

For example, the OCT system for generating a B-scan image of a target that has a surface and a depth may comprise a detector. The detector may comprise at least three pixels ("detector pixels"). The OCT system may have a configuration that, during operation, may illuminate and scans at least one physical position on the target surface; and may form sets of detector pixels. Each detector pixel set may comprise at least two detector pixels. The detector pixels forming the same detector pixel set may be adjacent to each other. The OCT system may have a configuration that, during operation, may form discretized OCT interference spectra on each detector pixel; and may generate at least two A-scans. Each A-scan may be generated from the discretized OCT interference spectra formed on each detector pixel. The OCT system may have a configuration that, during operation, may form at least two B-scans ("shaped B-scan") based on generated A-scans. The A-scans forming each shaped B-scan may be generated from the discretized OCT interference spectra formed on the detector pixels of the same detector pixel set. The OCT system may have a configuration that, during operation, may determine a maximum intensity of each shaped B-scan; may normalize each shaped B-scan ("normalized B-scan") by using the maximum intensity of the same shaped B-scan; and may form sets of pixels. Each pixel set may comprise one pixel ("B-scan pixel") from each normalized B-scan. The B-scan pixels of each pixel set may have the same position on all normalized B-scans. The OCT system may have a configuration that, during operation, may determine one intensity ("optimized intensity") for each pixel set by applying a mathematical operation to intensities of pixels forming the same pixel set. The mathematical operation may comprise a rank order filter, a mean filter, a multi-image deconvolution, or a combination thereof. The OCT system may have a configuration that, during operation, may generate a new B-scan ("new B-scan") based on the optimized intensities of the pixel sets.

For example, the OCT system for generating a B-scan image of a target that has a surface and a depth may have a configuration that, during operation may acquire at least two A-scans. Each acquired A-scan may be generated from discretized OCT interference spectra formed on a pixel of a detector. The detector may comprise at least three pixels ("detector pixels"). The at least two A-scans may be generated by forming sets of detector pixels. Each detector pixel set may comprise at least two detector pixels. The detector pixels forming the same detector pixel set may be adjacent to each other. The OCT system may have a configuration that, during operation, may form at least two B-scans ("shaped B-scan") based on the acquired A-scans. The A-scans forming each shaped B-scan may be generated from the discretized OCT interference spectra formed on the detector pixels of the same detector pixel set. The OCT system may have a configuration that, during operation, may determine a maximum intensity of each shaped B-scan; may normalize each shaped B-scan ("normalized B-scan") by using the maximum intensity of the same shaped B-scan; and may form sets of pixels. Each pixel set may comprise one pixel ("B-scan pixel") from each normalized B-scan. The B-scan pixels of each pixel set may have the same position on all normalized B-scans. The OCT system may have a configuration that, during operation, may determine one intensity ("optimized intensity") for each pixel set by applying a mathematical operation to intensities of pixels forming the same pixel set. The mathematical operation may comprise a rank order filter, a mean filter, a multi-image deconvolution, or a combination thereof. The OCT system may have a configuration that, during operation, may generate a new B-scan ("new B-scan") based on the optimized intensities of the pixel sets.

For example, the OCT system for generating a B-scan image of a target that has a surface and a depth may have a configuration that, during operation may acquire at least two B-scans ("shaped B-scans"). Each shaped B-scan may comprise at least two A-scans. Each A-scan may be generated from discretized OCT interference spectra formed on a pixel of a detector. The detector may comprise at least three pixels ("detector pixels"). The at least two A-scans may be generated by forming sets of detector pixels. Each detector pixel set may comprise at least two detector pixels. The detector pixels forming the same detector pixel set may be adjacent to each other. The A-scans forming each shaped B-scan may be generated from the discretized OCT interference spectra formed on the detector pixels of the same detector pixel set. The OCT system may have a configuration that, during operation, may determine a maximum intensity of each shaped B-scan; may normalize each shaped B-scan ("normalized B-scan") by using the maximum intensity of the same shaped B-scan; and may form sets of pixels. Each pixel set may comprise one pixel ("B-scan pixel") from each normalized B-scan. The B-scan pixels of each pixel set may have the same position on all normalized B-scans. The OCT system may have a configuration that, during operation, may determine one intensity ("optimized intensity") for each pixel set by applying a mathematical operation to intensities of pixels forming the same pixel set. The mathematical operation may comprise a rank order filter, a mean filter, a multi-image deconvolution, or a combination thereof. The OCT system may have a configuration that, during operation, may generate a new B-scan ("new B-scan") based on the optimized intensities of the pixel sets.

Example 1

This example demonstrates reduction of axial sidelobe noise by using the multi-shaping approach (i.e. shaping each raw A-scan by using at least two shaping functions) and generation of a new B-scan (i.e. an improved OCT image).

The multi-shaping approach was applied on three OCT datasets of imaging a 0.3-µm microbeads phantom, a zebrafish embryo and human retina, respectively. In this example, all B-scan images were smoothed by a 3×3 median filter, and displayed in a 50-dB dynamic range.

Figure 17:
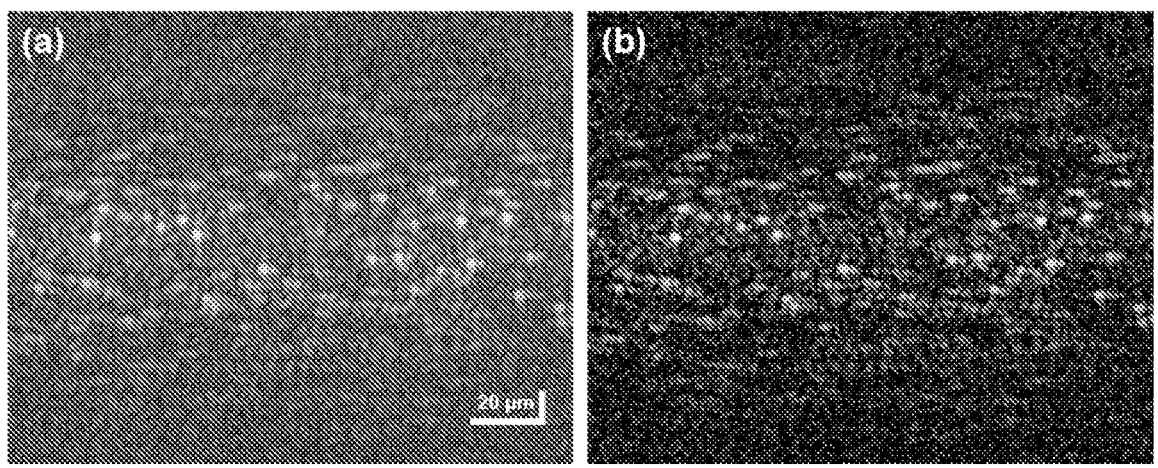
FIG. 17 shows OCT images of a 0.3-μm microbeads phantom with reduced sidelobe noise: (a) a B-scan image of microbeads with the standard Gaussian shaping, (b) an improved B-scan image of microbeads with the multi-shaping technique applied.

B-scan images of a 0.3-µm microbeads phantom, shown in FIG. 17, were acquired by an SD-OCT system. The comparison of FIGS. 17(a) and (b) reveals that the multi-shaping technique reduced the undesired background noise appearing in FIG. 17(a) and provided better visualization of individual beads in FIG. 17(b). The axial sidelobe of a single bead was reduced from −18 dB in FIG. 17(a) to −26 dB in FIG. 17(b).

Figure 18:
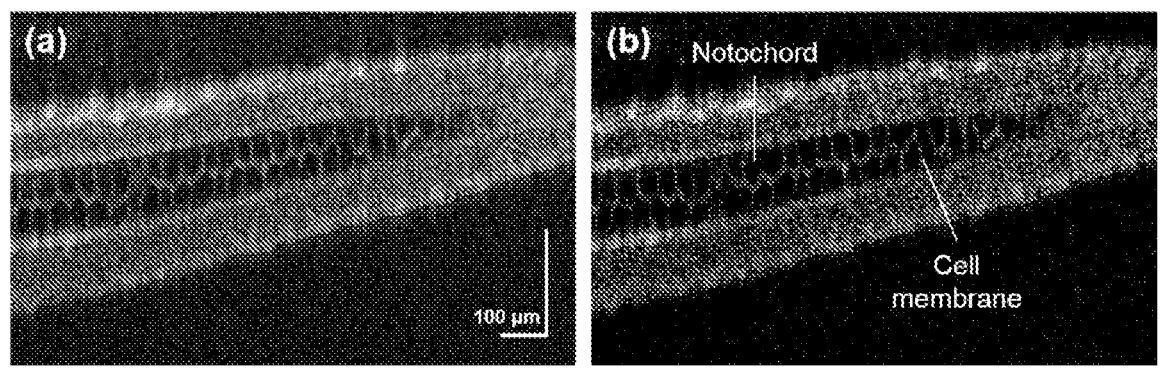
FIG. 18 shows OCT images of a 3-dpf zebrafish embryo with reduced sidelobe noise: (a) a B-scan image of the embryo's trunk with the standard Gaussian shaping, (b) an improved B-scan image of the embryo's trunk with the multi-shaping technique applied.

B-scan images of a zebrafish embryo, shown in FIG. 18, were acquired by an SD-OCT system. By applying the multi-shaping technique, the background inside the notochord became much cleaner, resulting in much better identification of the structure of cell boundaries inside. The B-scan image obtained without application of the multi-shaping technique is shown in FIG. 18(a). In the middle of the notochord, the features where two layers meet were more clearly resolved, as shown in FIG. 18(b). The average contrast of the sample region was 211% higher than the background region in FIG. 18(b), increasing from 91% in FIG. 18(a).

Figure 19:
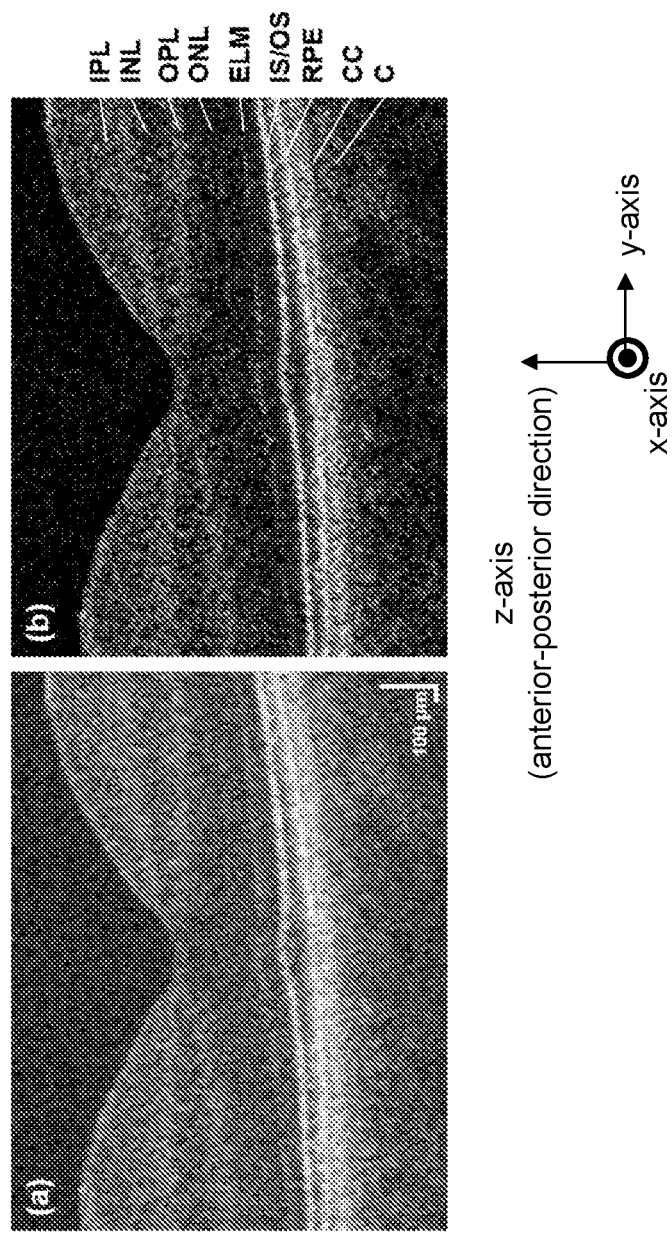
FIG. 19 shows OCT images of a human retina with reduced sidelobe noise: (a) a B-scan image of the retina with the standard Gaussian shaping, (b) an improved B-scan image of the retina with the multi-shaping technique applied. IPL: inner plexiform layer; INL: inner nuclear layer; OPL: outer plexiform layer; ONL: outer nuclear layer; ELM: external limiting membrane; IS/OS: junction between the inner and outer photoreceptors; RPE: retinal pigment epithelium; CC: choriocapillaris; C: choroid.

B-scan images of the retina from a healthy adult subject, shown in FIG. 19, were acquired by an SD-OCT system. Processed by using the multi-shaping technique, FIG. 19(b) had much lower noise in both sample and background regions. The improved B-scan image in FIG. 19(b) was better in resolving not only bright layers (IS/OS, RPE and CC), but also features within relative dim layers (OPL and ELM). Moreover, weak signals of the choroid (C) can be better identified, as they were not overwhelmed by the background noise in FIG. 19(a). The average contrast of the sample region was 41% higher than the background region in FIG. 19(a) and it was increased to 85% in FIG. 19(b).

Example 2

A mathematical operation, which may be used to process intensity values of selected pixels of B-scan images in a B-scan image cluster, may be a minimum rank order filter. By using the minimum rank order filter, better mainlobe resolution and sidelobe reduction may be achieved. For some improved B-scan image generations, however, the use of the minimum rank order filter may result in intensity loss and weakly scattering physical structures of the target may become even dimmer, reducing the quality of the B-scan image thereby generated.

Figure 20:
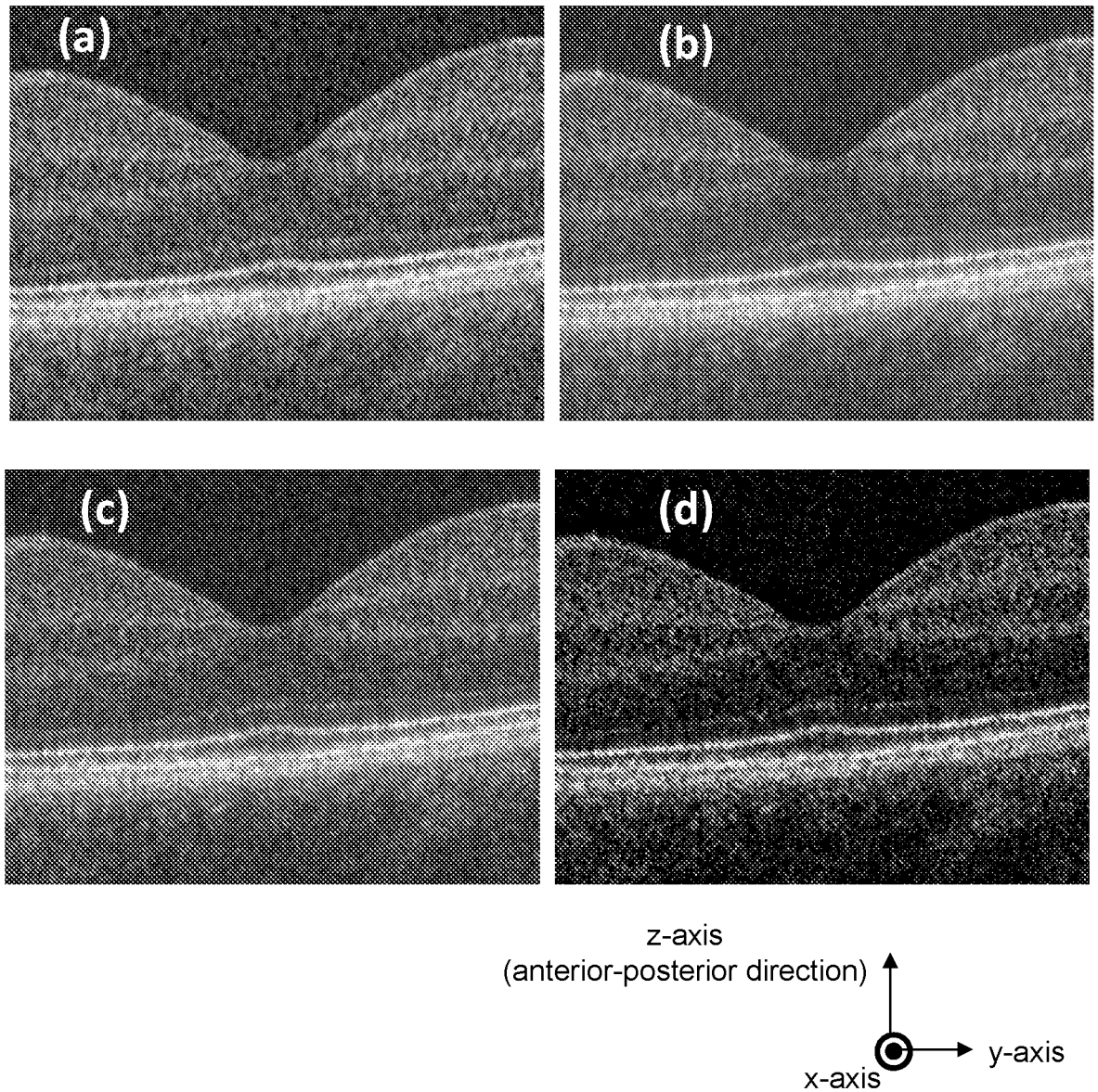
FIG. 20 shows OCTs image of a human retina: (a) a B-scan image of the retina formed without multi-shaping, (b) a B-scan image of the retina formed by multi-shaping and using a median filter, (c) a B-scan image of the retina formed by multi-shaping and using a rank order ($17^{th}$ smallest) filter, (d) a B-scan image of the retina formed by multi-shaping the raw B-scan and using a minimum filter. The retinal layers shown on these images can be identified by referring to the retinal layer labels of FIG. 19.

For example, some parts of the tissue structure around the ONL layer almost disappeared when the minimum filter was used as the mathematical operation in processing, as shown in FIG. 20 (d). By comparison, the tissue structure around the ONL layer appeared to have better contrast, as shown in FIG. 20 (a).

For such instances, the B-scan image quality may further be improved by applying a higher rank order filter, such as a median filter or a filter that has a rank in between the median filter and the minimum filter. The higher rank order filter may increase the intensity of the generated B-scan image and better preserve signals of the weakly scattering physical structure, but with slightly reduced mainlobe resolution and weaker sidelobe reduction. When higher rank order filters were used, the multi-shaped B-scan image quality may further be improved, as shown in FIG. 20 (b) where the B-scan image was generated by application of the median filter, and as shown in FIG. 20 (c) where the B-scan image was generated by application of the $17^{th}$ smallest rank order filter.

Example 3

While the multi-shaping technique may improve the quality of the OCT intensity images, it may also improve the quality of the OCT angiography images, because effective removal of angiographic noise from background regions may highly be dependent on the intensity thresholding determined by OCT intensity images.

Figure 21:
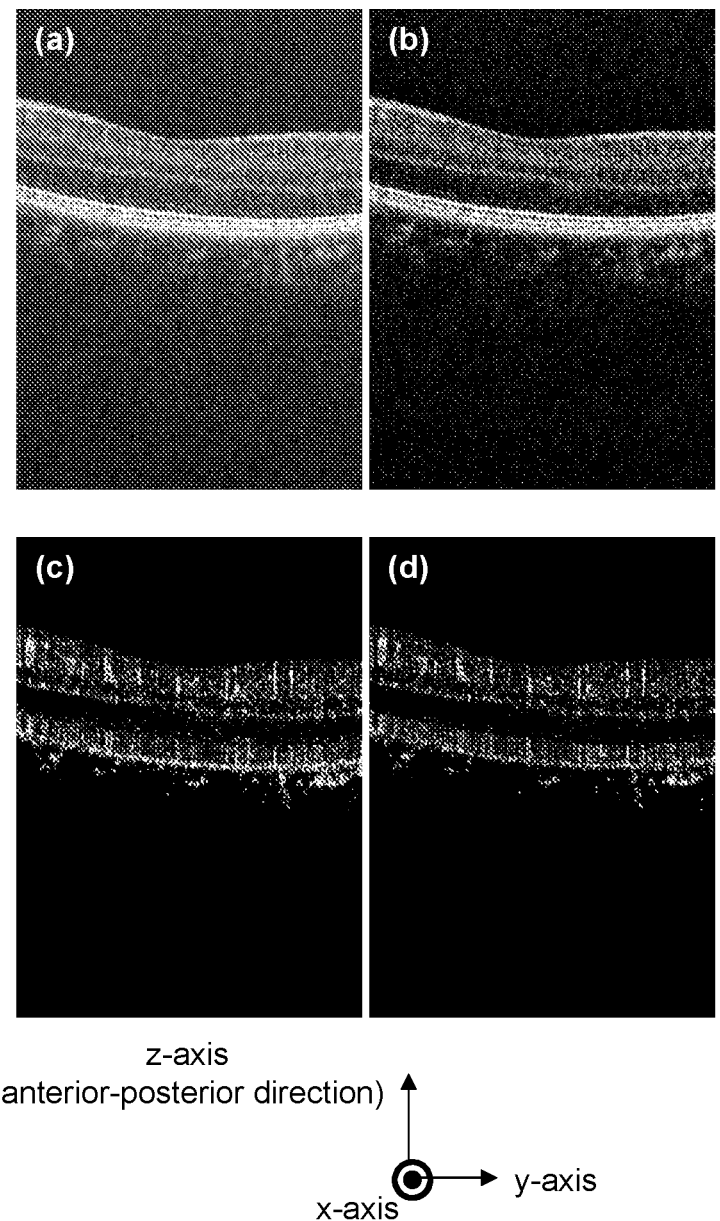
FIG. 21 shows an OCT image of a human retina: (a) a B-scan intensity image of the retina formed without multi-shaping, (b) a B-scan intensity image of the retina formed by multi-shaping, (c) a B-scan angiography image of the retina formed without multi-shaping, (d) a B-scan angiography image of the retina formed by multi-shaping.
Figure 22:
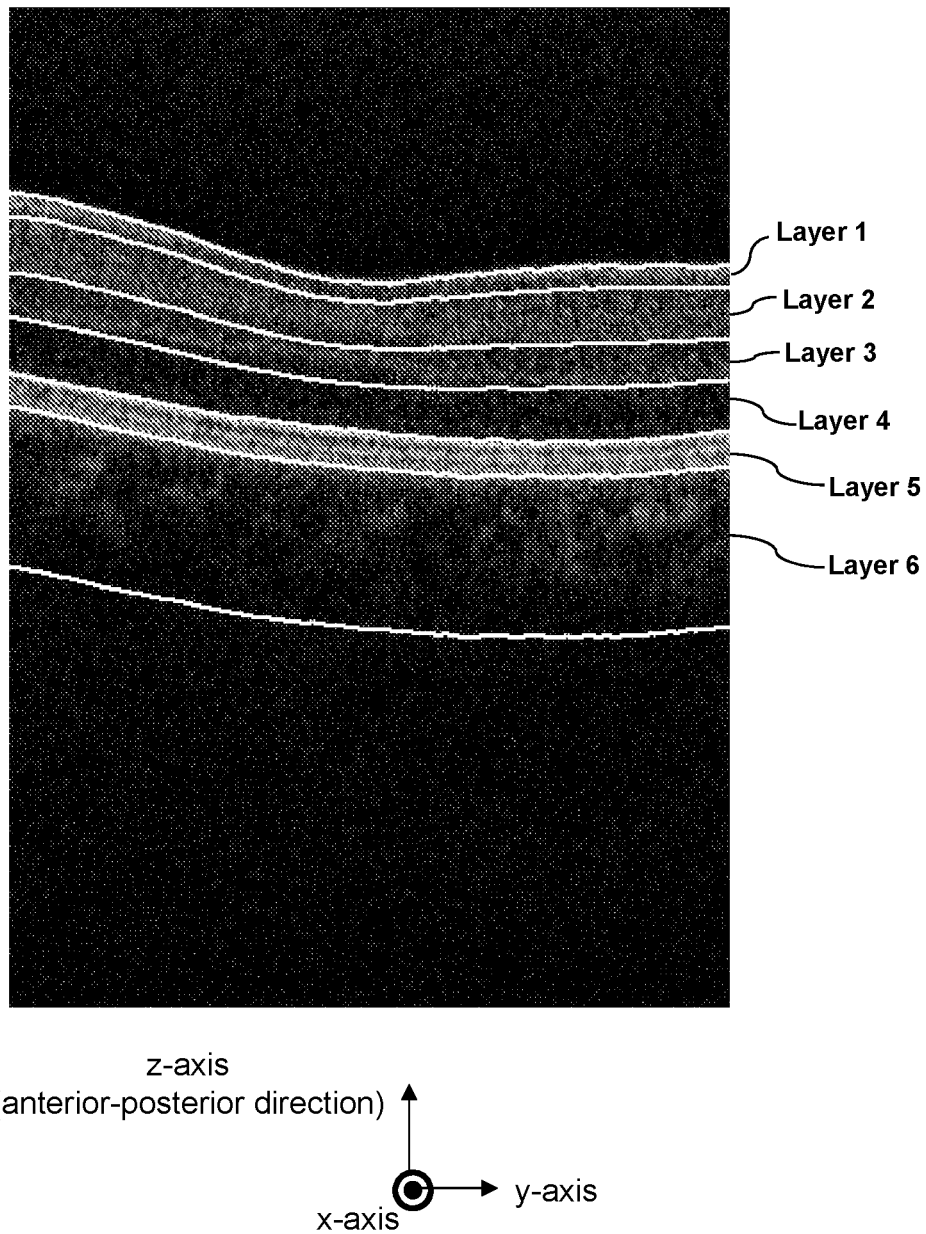
FIG. 22 shows an OCT image of a human retina: segmentation of a B-scan intensity image for en face visualization. The six segments are labeled as Layer 1 to Layer 6.
Figure 23:
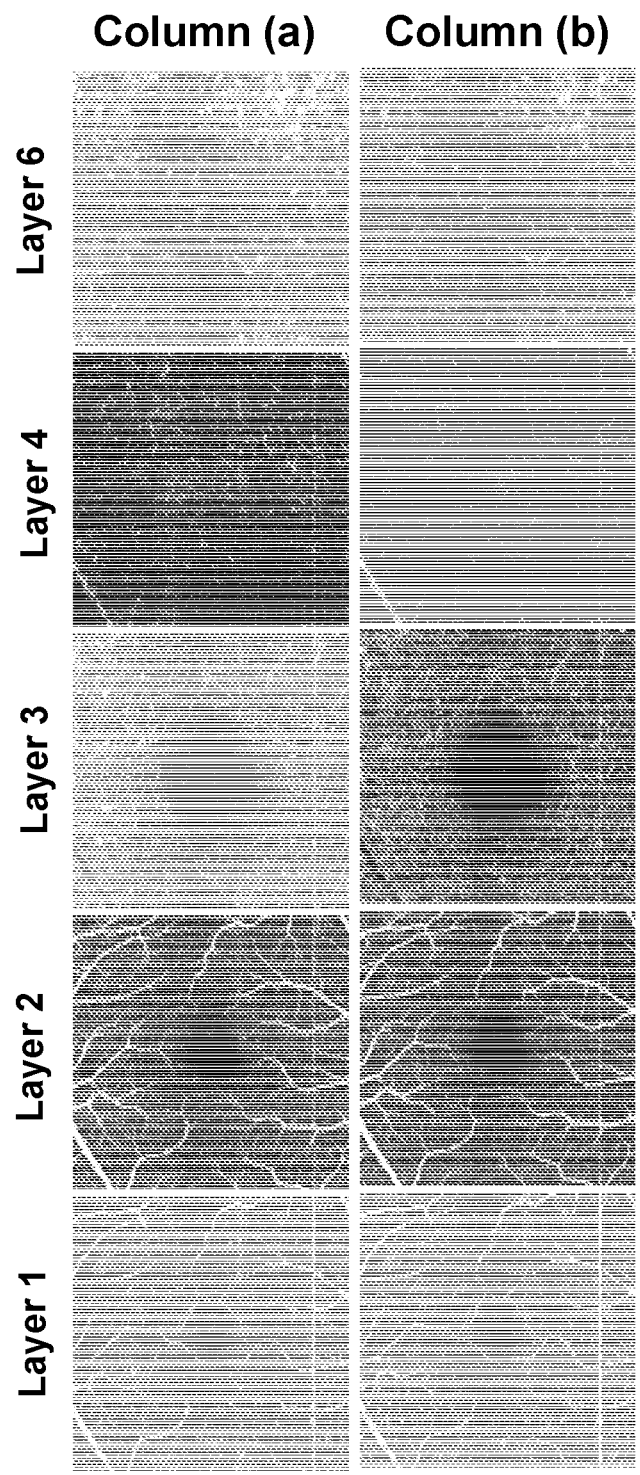
FIG. 23 shows en face angiography images of Layers 1-4 and Layer 6 of FIG. 22: column (a) en face angiography images formed without multi-shaping, column (b) en face angiography images formed by multi-shaping.

Suppression of sidelobe magnitude by multi-shaping leads to lower background noise and cleaner angiography images of higher contrast as a result. For example, the multi-shaping technique may improve the visualization of human retinal angiography image generated by a phase variance OCT (pvOCT) technique. As shown in FIGS. 21-23, blood vessels in less bright layers that tend to be affected by sidelobe artifacts may be better visualized, such as the ONL layer (layer 3), avascular zone (layer 4), and choroid region (layer 6).

The OCT methods compromising the multi-shaping and detector multi-apodization techniques disclosed above may be used for any OCT related application. For example, the methods may be used in forming larger field of view OCT images of the physical object. The methods may be incorporated into methods and systems related to OCT based angiography.

The OCT systems of this disclosure may be used to diagnose any health condition. For example, the OCT system may be used to diagnose any health condition of any mammal. For example, the OCT system may be used to diagnose any health condition of a human. Examples of the health condition may comprise a disease, a congenital malformation, a disorder, a wound, an injury, an ulcer, an abscess, or the like. The health condition may be related to a tissue. The tissue may be any tissue. For example, the tissue may comprise a retina. For example, the choroidal vasculature may be identified in more detail. The OCT methods comprising the multi-shaping and detector multi-apodization techniques may also be used in diagnosis and/or treatment of health conditions such as diseases. For example, the methods may be used in characterization of retinal health.

The OCT system disclosed above may provide any information related to the physical object. For example, this system, which may use the multi-shaping and detector multi-apodization techniques, may provide 2D (i.e. cross-sectional) images, en-face images, 3D images, metrics related to a health condition, and the like. This system may be used with any other system. For example, the OCT system may be used with an ultrasound device, or a surgical system for diagnostic or treatment purposes. The OCT system may be used to analyze any physical object. For example, the OCT system may be used in analysis, e.g. formation of images, of, for example, any type of life forms and inanimate objects. Examples of life forms may be animals, plants, cells or the like.

Unless otherwise indicated, the image generation system 140 that has been disclosed herein may be implemented with a computer system configured to perform the functions that have been described herein for this system. The computer system includes one or more processors, tangible memories (e.g., random access memories (RAMs), read-only memories (ROMs), and/or programmable read only memories (PROMS)), tangible storage devices (e.g., hard disk drives, CD/DVD drives, and/or flash memories), system buses, video processing components, network communication components, input/output ports, and/or user interface devices (e.g., keyboards, pointing devices, displays, microphones, sound reproduction systems, and/or touch screens).

The computer system for image generation system 140 may include one or more computers at the same or different locations. When at different locations, the computers may be configured to communicate with one another through a wired and/or wireless network communication system.

The computer system may include software (e.g., one or more operating systems, device drivers, application programs, and/or communication programs). When software is included, the software includes programming instructions and may include associated data and libraries. When included, the programming instructions are configured to implement one or more algorithms that implement one or more of the functions of the computer system, as recited herein. The description of each function that is performed by each computer system also constitutes a description of the algorithm(s) that performs that function.

The software may be stored on or in one or more non-transitory, tangible storage devices, such as one or more hard disk drives, CDs, DVDs, and/or flash memories. The software may be in source code and/or object code format. Associated data may be stored in any type of volatile and/or non-volatile memory. The software may be loaded into a non-transitory memory and executed by one or more processors.

A better diagnosis of health of a tissue may be reached by using the improved images generated by the OCT systems of this disclosure.

Any combination of methods, devices, optical components, systems, and features/configurations disclosed above are within the scope of this disclosure.

In this disclosure, the indefinite article "a" and phrases "one or more" and "at least one" are synonymous and mean "at least one".

All articles, patents, patent applications, and other publications that have been cited in this disclosure are incorporated herein by reference.

The components, steps, features, objects, benefits, and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, objects, benefits, and/or advantages. These also include embodiments in which the components and/or steps are arranged and/or ordered differently.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The phrase "means for" when used in a claim is intended to and should be interpreted to embrace the corresponding structures and materials that have been described and their equivalents. Similarly, the phrase "step for" when used in a claim is intended to and should be interpreted to embrace the corresponding acts that have been described and their equivalents. The absence of these phrases from a claim means that the claim is not intended to and should not be interpreted to be limited to these corresponding structures, materials, or acts, or to their equivalents.

Relational terms such as "first" and "second" and the like may be used solely to distinguish one entity or action from another, without necessarily requiring or implying any actual relationship or order between them. The terms "comprises," "comprising," and any other variation thereof when used in connection with a list of elements in the specification or claims are intended to indicate that the list is not exclusive and that other elements may be included. Similarly, an element preceded by an "a" or an "an" does not, without further constraints, preclude the existence of additional elements of the identical type.

The abstract is provided to help the reader quickly ascertain the nature of the technical disclosure. It is submitted with the understanding that it will not be used to interpret or limit the scope or meaning of the claims. In addition, various features in the foregoing detailed description are grouped together in various embodiments to streamline the disclosure. This method of disclosure should not be interpreted as requiring claimed embodiments to require more features than are expressly recited in each claim. Rather, as the following claims reflect, inventive subject matter lies in less than all features of a single disclosed embodiment. Thus, the following claims are hereby incorporated into the detailed description, with each claim standing on its own as separately claimed subject matter.

The scope of protection is limited solely by the claims that now follow. That scope is intended and should be interpreted to be as broad as is consistent with the ordinary meaning of the language that is used in the claims when interpreted in light of this specification and the prosecution history that follows, except where specific meanings have been set forth, and to encompass all structural and functional equivalents.

None of the claims are intended to embrace subject matter that fails to satisfy the requirement of Sections 101, 102, or 103 of the Patent Act, nor should they be interpreted in such a way. Any unintended coverage of such subject matter is hereby disclaimed. Except as just stated in this paragraph, nothing that has been stated or illustrated is intended or should be interpreted to cause a dedication of any component, step, feature, object, benefit, advantage, or equivalent to the public, regardless of whether it is or is not recited in the claims.

The invention claimed is:

1. An optical coherence tomography (OCT) system for generating a B-scan image of a target that has a surface and a depth, comprising:
    an optical system; and
    an image generation system;
    wherein:
        the optical system comprises an illumination source, a beam splitter, a target arm, a reference arm, and an optical detection system;
        the image generation system comprises a control unit, a processing unit, a memory unit, and a display unit; and
        the OCT system has a configuration that, during operation:
            illuminates and scans the target;
            forms discretized OCT interference spectra;
            generates at least two raw A-scans;
            shapes each raw A-scan by using at least two different shaping functions for each raw A-scan to form at least two shaped A-scans for each raw A-scan;
            forms at least two B-scans ("shaped B-scans"), wherein the shaped A-scans forming the same shaped B-scan are shaped with the same shaping function;
            determines a maximum intensity of each shaped B-scan;
            normalizes each shaped B-scan ("normalized B-scan") by using the maximum intensity of the same shaped B-scan;
            forms sets of pixels, wherein each pixel set comprises one pixel ("B-scan pixel") from each normalized B-scan, wherein the B-scan pixels of each pixel set have the same position on all normalized B-scans;
            determines one intensity ("optimized intensity") for each pixel set by applying a mathematical operation to intensities of pixels forming the same pixel set; wherein the mathematical operation comprises a rank order filter, a mean filter, a multi-image deconvolution, or a combination thereof;
            generates a new B-scan ("new B-scan") based on the optimized intensities of the pixel sets; and
            displays the new B-scan on the image generation system's display unit.

2. The OCT system of claim 1, wherein the shaping function comprises a function that is zero-valued outside of a chosen interval.

3. The OCT system of claim 1, wherein the shaping function comprises a window function, a Gaussian function, or a combination thereof.

4. The OCT system of claim 1, wherein the mathematical operation comprises a rank order filter that is a minimum filter, a median filter, a rank order filter that has a rank between that of the minimum filter and the median filter, or a combination thereof.

5. The OCT system of claim 1, wherein the mathematical operation comprises a mean filter that is an arithmetic mean, a weighted mean, a geometric mean, a harmonic mean, a quadratic mean, a logarithmic mean, or a combination thereof.

6. The OCT system of claim 1, wherein the OCT system has a configuration that, during operation, smooths the new B-scan by using a digital smoothing filter.

7. The OCT system of claim 1, wherein the OCT system has a configuration that, during operation, smooths the new B-scan by using a digital smoothing filter; and wherein the digital smoothing filter comprises a linear smoothing filter, a non-linear smoothing filter, or a combination thereof.

8. The OCT system of claim 1, wherein the OCT system has a configuration that, during operation, smooths the generated new B-scan by using a digital smoothing filter; and
wherein the digital smoothing filter comprises a median filter, a Gaussian filter, or a combination thereof.

9. The OCT system of claim 1, wherein the optical detection system comprises a spectrometer, wherein the spectrometer comprises a detector, and wherein the detector comprises at least three pixels ("detector pixels").

10. The OCT system of claim 9, wherein the the spectrometer further comprises an optical grating, a first optical lens between the beam splitter and the grating, and a second optical lens between the optical grating and the detector; and wherein the first lens, the grating and the second lens have a configuration that projects an interfered light beam formed by the beam splitter on the at least three pixels.

11. The OCT system of claim 9, wherein the OCT system has a configuration that, during operation:
    illuminates and scans at least one physical position on the target surface;
    forms sets of detector pixels, wherein each detector pixel set comprises at least two detector pixels, and wherein the detector pixels forming the same detector pixel set are adjacent to each other;
    forms discretized OCT interference spectra on each detector pixel;
    generates at least two A-scans, wherein each A-scan is generated from the discretized OCT interference spectra formed on each detector pixel;
    forms at least two B-scans ("shaped B-scans") based on the generated A-scans, wherein the A-scans forming each shaped B-scan are generated from the discretized OCT interference spectra formed on the detector pixels of the same detector pixel set;
    determines a maximum intensity of each shaped B-scan;
    normalizes each shaped B-scan ("normalized B-scan") by using the maximum intensity of the same shaped B-scan;
    forms sets of pixels, wherein each pixel set comprises one pixel ("B-scan pixel") from each normalized B-scan, and wherein the B-scan pixels of each pixel set have the same position on all normalized B-scans;
    determines one intensity ("optimized intensity") for each pixel set by applying a mathematical operation to intensities of pixels forming the same pixel set; wherein the mathematical operation comprises a rank order filter, a mean filter, a multi-image deconvolution, or a combination thereof;
    generates a new B-scan ("new B-scan") based on the optimized intensities of the pixel sets; and
    displays the new B-scan on the image generation system's display unit.

12. The OCT system of claim 11, wherein the mathematical operation comprises a rank order filter that is a minimum filter, a median filter, a rank order filter that has a rank between that of the minimum filter and the median filter, or a combination thereof.

13. The OCT system of claim 11, wherein the mathematical operation comprises a mean filter that is an arithmetic mean, a weighted mean, a geometric mean, a harmonic mean, a quadratic mean, a logarithmic mean, or a combination thereof.

14. The OCT system of claim 11, wherein the OCT system has a configuration that smooths the generated new B-scan by using a digital smoothing filter.

15. The OCT system of claim 11, wherein the OCT system has a configuration that smooths the generated new B-scan by using a digital smoothing filter; and wherein the digital smoothing filter comprises a linear smoothing filter, a non-linear smoothing filter, or a combination thereof.

16. The OCT system of claim 11, wherein the OCT system has a configuration that smooths the generated new B-scan; and wherein the digital smoothing filter comprises a median filter, a Gaussian filter, or a combination thereof.

\* \* \* \* \*